United States Patent [19]

Coy et al.

[11] Patent Number: 5,597,894
[45] Date of Patent: Jan. 28, 1997

[54] MULTI-TYROSINATED SOMATOSTATIN ANALOGS

[75] Inventors: David H. Coy, New Orleans; Eugene A. Woltering, Kenner, both of La.; M. Sue O'Dorisio; Thomas M. O'Dorisio, both of Columbus, Ohio; William A. Murphy, Slidell, La.

[73] Assignees: The Louisiana State University Medical Center Foundation, New Orleans, La.; Children's Hospital, Inc., Columbus, Ohio; The Administrators of the Tulane Educational Fund, New Orleans, La.; The Ohio State University Research Foundation, Columbus, Ohio

[21] Appl. No.: 462,223

[22] Filed: Jun. 5, 1995

[51] Int. Cl.$^6$ .................... A61K 38/00; C07K 5/00; C07K 7/00

[52] U.S. Cl. .................... 530/311; 530/317; 530/324; 530/328; 530/327

[58] Field of Search .................... 530/311, 317, 530/324, 325, 326, 327, 328; 514/11, 12, 13, 14, 15

[56] References Cited

U.S. PATENT DOCUMENTS

| | | | |
|---|---|---|---|
| 4,133,782 | 1/1979 | Vale, Jr. et al. | 260/8 |
| 4,146,612 | 3/1979 | Veber | 424/177 |
| 4,190,648 | 2/1980 | Veber | 424/177 |
| 4,211,693 | 7/1980 | Rivier et al. | 260/112.5 S |
| 4,224,190 | 9/1980 | Villadsen et al. | 252/463 |
| 4,230,617 | 10/1980 | Sarantakis | 530/311 |
| 4,235,886 | 11/1980 | Freidinger et al. | 424/177 |
| 4,238,481 | 12/1980 | Rink et al. | 424/177 |
| 4,291,022 | 9/1981 | Sandrin et al. | 424/177 |
| 4,310,518 | 1/1982 | Freidinger et al. | 424/177 |
| 4,316,890 | 2/1982 | Kamber et al. | 424/177 |
| 4,328,214 | 5/1982 | Rink et al. | 424/177 |
| 4,358,439 | 11/1982 | Sieber et al. | 424/177 |
| 4,360,516 | 11/1982 | Freidinger et al. | 514/11 |
| 4,369,179 | 1/1983 | Rink et al. | 424/177 |
| 4,395,403 | 7/1983 | Bauer et al. | 424/177 |
| 4,435,385 | 3/1984 | Bauer et al. | 424/177 |
| 4,485,101 | 11/1984 | Coy et al. | 424/177 |
| 4,486,415 | 12/1984 | Freidinger | 424/177 |
| 4,522,813 | 6/1985 | Nutt | 514/11 |
| 4,585,755 | 4/1986 | Morgan et al. | 514/11 |
| 4,603,120 | 7/1986 | Kamber | 514/11 |
| 4,650,787 | 3/1987 | Schally et al. | 514/11 |
| 4,684,620 | 8/1987 | Hruby et al. | 514/11 |
| 4,725,577 | 2/1988 | Schally et al. | 514/11 |
| 4,801,803 | 1/1989 | Denen et al. | 250/336.1 |
| 4,853,371 | 8/1989 | Coy et al. | 514/12 |
| 4,871,717 | 10/1989 | Coy et al. | 514/11 |
| 4,889,991 | 12/1989 | Ramsey et al. | 250/336.1 |
| 4,904,642 | 2/1990 | Coy et al. | 514/11 |
| 5,008,546 | 4/1991 | Mazziotta et al. | 250/366 |
| 5,070,878 | 12/1991 | Denen | 128/659 |
| 5,462,926 | 10/1995 | Coy et al. | 514/16 |

FOREIGN PATENT DOCUMENTS

| | | | |
|---|---|---|---|
| 0203031 | 11/1986 | European Pat. Off. | C07K 7/06 |
| 0363589 | 8/1988 | European Pat. Off. | C07K 7/26 |
| 0505680A1 | 9/1992 | European Pat. Off. | C07K 7/02 |
| 0515313 | 11/1992 | European Pat. Off. | C07K 7/26 |
| 0588754A1 | 3/1994 | European Pat. Off. | A61K 49/02 |
| 0607103 | 7/1994 | European Pat. Off. | C07K 7/26 |
| WO91/01144 | 2/1991 | WIPO | A61K 43/00 |
| WO91/09056 | 6/1991 | WIPO | C07K 7/26 |

OTHER PUBLICATIONS

Sayers et al., "An improved technique for the preparation of isolated rat adrenal cells: a sensitive, accurate and specific method for the assay of ACTH," 1971, *Endocrinology* 88:1063–1068.

Munson et al., "ligand: a versatile computerized approach for characterization of Ligand–binding systems," 1980, *Anal. Biochem.* 107:220–239.

McPherson, "Analysis of radioligand binding experiements," 1985, *J. of Pharm. Meth.* 14:213–228.

Ben-Jonathan et al., "Optimization of culture conditions for short–term pituitary cell culture," 1983, *Methods in Enzymology* 103:249–257.

(List continued on next page.)

Primary Examiner—Avis M. Davenport
Attorney, Agent, or Firm— Fish & Richardson P.C.

[57] ABSTRACT

Disclosed are methods and compositions for the diagnosis and treatment of diseases associated with aberrant expression of a somatostatin receptor (e.g., cancer) or with increased production of a factor regulatable by somatostatin (e.g., acromegaly). The compounds of the invention are of the general formulae:

a) $(Y)_{n+1}P$,
b) $(Y)_n$—Ala—Y—P, or

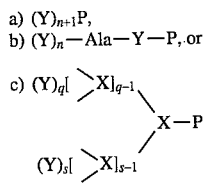

wherein
P is a somatostatin peptide analog which binds to a somatostatin receptor,
Y is D-tyrosine, L-tyrosine, or desamino-tyrosine,
n is an integer from 1 to 32, inclusive,
each q, independently, is an integer from 1 to 32, inclusive, and each s, independently, is an integer from 1 to 32, inclusive, where q and s can be the same or different, and
X is of the formula $$D-NH_2-CH(CH_2)_m NH_2-CO_2H \text{ or}$$

$$L-NH_2-CH(CH_2)_m NH_2-CO_2H,$$

wherein m is an integer from 1 to 10, inclusive.

12 Claims, 2 Drawing Sheets

OTHER PUBLICATIONS

Hoefer et al., "Prolactin secretion by cultured anterior pituitary cells: influence of culture conditions and endocrine status of the pituitary donor," 1984, *Mol. Cell. Endocrin.* 35:229–235.

Hanks et al., "Peptides and the blood–brain barrier: Lipophilicity as a predictor of permeability," 1985, *Brain Res. Bull.* 15:287–292.

Heiman et al., "An extremely sensitive in vitro model for elucidating structure–activity relationships of growth hormone–releasing factor analogs," 1985, *Endocrinology* 116(1)410–415.

Van Binst et al., "Backbone modifications in somatostatin analogues: relation between conformation and activity," 1992, *Peptide Res.* 5(1):8–13.

Prevost et al., "Molecular heterogeneity of somatostatin analogue BIM–23014C receptors in human breast carcinoma cells using the chemical cross–linking assay," 1992, *Cancer Res.* 52:843–850.

Yamada et al., "Cloning and functional characterization of a family of human and mouse somatostatin receptors expressed in brain, gastrointestinal tract, and kidney," 1992, *Proc. Natl. Acad. Sci. USA* 89:251–255.

Raynor et al., "Cloned somatostatin receptors: identification of subtype–selective peptides and demonstration of high affinity binding of linear peptides," 1993, *Mol. Pharmacol.* 43:838–844.

Krenning et al., "Somatostatin receptor scintigraphy with [$^{111}$in–DTPA–d–Phe$^{1}$]– and [$^{123}$I–Tyr$^{3}$]–octreotide: the Rotterdam experience with more than 1000 patients," 1993, *Eur. J. Nuc. Med.* 20(8):716–731.

Rohrer et al., "Cloning and characterization of a fourth human somatostatin receptor," 1993, *Proc. Natl. Acad. Sci. USA* 90:4196–4200.

O'Dorisio et al., "Characterization of somatostatin receptors on human neuroblastoma tumors," 1994, *Cell Growth and Differentiation* 5:1–8.

Patel et al., "All five cloned human somatostatin receptors (hSSTR1–5) are functionally coupled to adenylyl cyclase," 1994, *Biochem. Biophys. Res. Commun.* 198(2):605–612.

Fisher et al., "Radiation dosimetry for radioimmunotherapy," 1994, *Cancer* 73(3):905–911.

Reubi et al., "Expression and localization of somatostatin receptor SSTR1, SSTR2, and SSTR3 messenger RNAs in primary human tumors using in Situ hybridization," 1994, *Cancer Res.* 54:3455–3459.

MULTI-TYROSINATED SOMATOSTATIN ANALOGS

STATEMENT AS TO FEDERALLY SPONSORED RESEARCH

This invention was made at least in part with funds from a Federal government grant from the National Cancer Institute, grant no. RO1 CA 64177. The government may have certain rights in the invention.

BACKGROUND OF THE INVENTION

This invention relates to the diagnosis and treatment of tumors having peptide-specific surface receptors.

Despite the advances in diagnosis and treatment of cancer, surgery remains the most reliable and effective long-term treatment of some types of cancer. The success of surgery is limited by precise and complete preoperative or intraoperative localization of tumors, an imprecise and incomplete assessment of the disease occurs in 20% to 40% of cancer cases. While various preoperative imaging techniques are available, the sensitivity of these techniques is proportional to tumor size. For example, the lower limit of resolution in CT scanning is 0.8 cm to 1.0 cm. Superselective angiography is more successful in tumor localization, but requires highly experienced technical expertise. Tumor localization techniques which do not rely on imaging, such as percutaneous transhepatic portal venous sampling (PTPVS), have been used successfully to regionally localize small functional tumors undetected by other methods. Still, these tumor localization methods are limited. For example, PTPVS does not routinely allow the individual assessment of nodal positivity or negativity and may not detect multicentric tumors.

When preoperative tumor localization fails, the clinician must next resort to exploratory surgery combined with intraoperative tumor localization and resection. Aggressive intraoperative localization is accomplished with a combination of ultrasound, palpation, and endoscopic or laparoscopic techniques. While these techniques allow the detection of small tumors undetected by available preoperative localization techniques, small tumors outside of the organs inspected may remain undetected. Moreover, morbidity resulting from exploratory surgery increases as more tissue is disturbed.

A variety of cancers, including both endocrine and non-endocrine tumors, express somatostatin receptors. Five human somatostatin receptors have been identified and cloned. Expression of these five receptor subtypes varies with tissue types. Somatostatin receptor subtype 2 is expressed on a wide variety of tumor types. Tables 1A and 1B provide a summary of somatostatin receptor expression in both normal and tumor tissues.

TABLE 1A

Somatostatin Receptor Subtype Expression in Normal Human Tissue

| Normal Human Tissue | Receptor Subtype | Reference |
| --- | --- | --- |
| Frontal Cortex | SST2, SST1, SST3, SST5 | Yamada et al., Proc. Natl. Acad. Sci. USA, 89:251–255, 1992; Rohrer et al., Proc. Natl. Acad. Sci. USA, 90:4196–4200, 1993 |
| Liver | SST2 (low) | Yamada et al., supra |
| Lung | SST1 | Rohrer et al., supra |
| Stomach | SST1 | Yamada et al., supra |
| Intestine (jejunum) | SST1 | Yamada et al., supra |
| Pancreas | SST1, SST3 | Yamada et al., supra |
| Colon | SST1 (low) SST2 (low) | Yamada et al., supra |
| Kidney | SST2 | Yamada et al., supra |

TABLE 1B

Somatostatin Receptor Subtype Expression in Human Tumor Tissue

| Human Tumor Tissue | Receptor Subtype | Reference |
| --- | --- | --- |
| Lung | SST2 | Patel et al., Biochem. Biophys. Res. Commun., 198:605–612, 1994 |
| Carcinoid | SST2, SST1, SST3 | Patel et al., supra |
| Insulinoma | SST3 | Reubi et al., Cancer Res., 54:3455–3459, 1994 |
| ACTH Secreting | SST1, SST2 | Reubi et al., supra |
| CLL | SST2 | Patel et al., supra |
| Neuroblastoma | SST2 | Patel et al., supra |
| Breast | SST2 | Patel et al., supra |
| Colon | SST1 | Yamada et al., Proc. Natl. Acad. Sci. USA, 89:251–255, 1992 |
| Hepatoma | SST2 | Yamada et al., supra |
| Pituitary Prolactinoma | SST2, SST3 | Reubi et al., supra |
| Pituitary Adenoma | SST2, SST1, SST3 | Patel et al., supra; Reubi et al., supra |
| Meningioma | SST2 | Patel et al., supra |

Endogenously produced somatostatin inhibits release of several pituitary and intestinal factors that regulate cell proliferation, cell motility, and/or secretion including growth hormone, adrenocorticotropin hormone, prolactin, thyroid stimulating hormone, insulin, glucagon, motilin, gastric inhibitory peptide (GIP), vasoactive intestinal peptide (VIP), secretin, cholecystokinin, bombesin, gastrin releasing peptide (GRP), gastrin, adrenocorticotropic hormone (ACTH), thyroid releasing hormone (TRH), choleocystokinin (CCK), aldosterone, pancreatic polypeptide (PP), cytokines (e.g., interleukins, interferons), growth factors (e.g., epidermal growth factor, nerve growth factor), and vasoactive amines (e.g., serotonin). Several of these factors are implicated in regulation of normal cell proliferation, as well as in tumor cell proliferation and/or metastasis. For example, GRP stimulates proliferation of normal and malignant intestinal epithelial cells, stimulates the proliferation of normal bronchial epithelial cells, and is an autocrine growth factor in small cell lung carcinoma.

Somatostatin-14 (S-14) and somatostatin-28 (S-28) are the two principal forms of native somatostatin. S-14 is a 14-amino acid peptide having the sequence Ala-Gly-Cys-Lys-Asn-Phe-Phe-Trp-Lys-Thr-Phe-Thr-Ser-Cys (SEQ ID NO:1). The amino acid sequence of S-14 is highly conserved among vertebrate species. S-14 has a cyclic molecular structure stabilized by a disulfide bond between $Cys_3$ and $Cys_{14}$ (the cysteines at positions 3 and 14 from the N-terminus) and by hydrogen and hydrophobic bonds. Four amino acids within the ring structure of somatostatin, $Phe_7$-$Trp_8$-$Lys_9$-$Thr_{10}$ (SEQ ID NO:2), are primarily responsible for receptor binding and biological activity, while the residues $Trp_8$-$Lys_9$ are predominate in receptor binding. S-28 is a 28-amino acid peptide and contains the amino acid sequence of S-14 with an additional 14 amino acids extending from the N-terminus. The structural differences in S-14 and S-28 influence the relative degrees of inhibitory activity on the biological functions regulated by somatostatin.

A variety of somatostatin peptide analogs have been produced by elimination of amino acids that are not absolutely required for activity and/or substitution of the native L-amino acids with the corresponding D-amino acid isomers. Thus, some of these analogs are longer acting, more potent receptor agonists than native somatostatin, due in part to the resistance of D-amino acids to enzyme degradation. For example, the synthetic somatostatin analog octreotide acetate, which has the amino acid sequence D-Phe-Cys-Phe-D-Trp-Lys-Thr-Cys-Thr(ol) (SEQ ID NO:3), is 45 to 70 times more potent than native somatostatin in inhibition of growth factor release. LANREOTIDE™, a synthetic somatostatin octapeptide analog having the amino acid sequence Dβ-Nal-Cys-Tyr-D-Trp-Lys-Val-Cys-Thr($NH_2$) (SEQ ID NO:4), is 20 to 50 times more potent than native somatostatin.

The use of somatostatin analogs in diagnosis and therapy is limited by the relatively short half-life of these analogs in vivo. Moreover, tumor localization techniques using detectably labeled somatostatin analogs are limited by the amount of detectable label that can be associated with each analog, the strength of the signal generated per analog molecule, and the sensitivity of available label detection techniques. There is a clear need in the field for both diagnostic and therapeutic methods which allow for highly specific and sensitive identification of tumor cells, as well as less invasive cancer therapy regimens.

SUMMARY OF THE INVENTION

It has been discovered that somatostatin peptide analogs can be modified by the addition of N-terminal amino acid extensions without impairing the ability of the compound to bind to somatostatin receptors. The N-terminal extensions can be linear or branched, and can be formulated to include multiple L-, D-, or desamino-tyrosine residues.

Accordingly, the invention features methods and compositions for the diagnosis and treatment of diseases associated with (1) aberrant expression of a somatostatin receptor (e.g., cancer), or (2) increased production of a factor(s) regulatable by somatostatin (e.g., acromegaly).

In one aspect, the invention features a compound of the formula:

a) $(Y)_{n+1}P$,
b) $(Y)_n$—Ala—Y—P, or c) 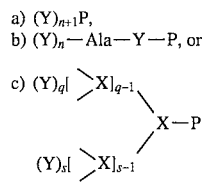

wherein P is a somatostatin peptide analog which binds to a somatostatin receptor, Y is D-tyrosine, L-tyrosine, or desamino-tyrosine, n is an integer from 1 to 32, inclusive, each q, independently, is an integer from 1 to 32, inclusive, and each s, independently, is an integer from 1 to 32, inclusive, where q and s can be the same or different, and X has the formula D—$NH_2$—CH($CH_2$)$_m$$NH_2$—$CO_2$H or L—$NH_2$—CH($CH_2$)$_m$$NH_2$—$CO_2$H, wherein m is an integer from 1 to 10, inclusive.

Preferably, P is of the formula:
a) Cys-Tyr-D-Trp-Lys-Val-Cys-Thr-$NH_2$;
b) Cys-Phe-D-Trp-Lys-Thr-Cys-Thr-$NH_2$; or
c) Cys-Tyr-D-Trp-Lys-Thr-Cys-Thr(ol).

In other preferred embodiments, X is lysine. Preferably, the compound contains at least one halogen atom bound to a tyrosine (Y in the formula above) of the compound. Preferably, the halogen atom is radioactive.

a) D—Tyr—Cys—Tyr—D—Trp—Lys—Val—Cys—Thr—$NH_2$, b) Tyr—D—Tyr—Cys—Phe—D—Trp—Lys—Thr—Cys—Thr—$NH_2$, c) Tyr—Ala—D—Tyr—Cys—Tyr—D—Trp—Lys—Val—Cys—Thr—$NH_2$, d) Tyr—D—Tyr—Cys—Tyr—D—Trp—Lys—Val—Cys—Thr—$NH_2$, e) D—Tyr—Tyr—Tyr—D—Tyr—Cys—Phe—D—Trp—Lys—Thr—Cys—Thr—$NH_2$, or

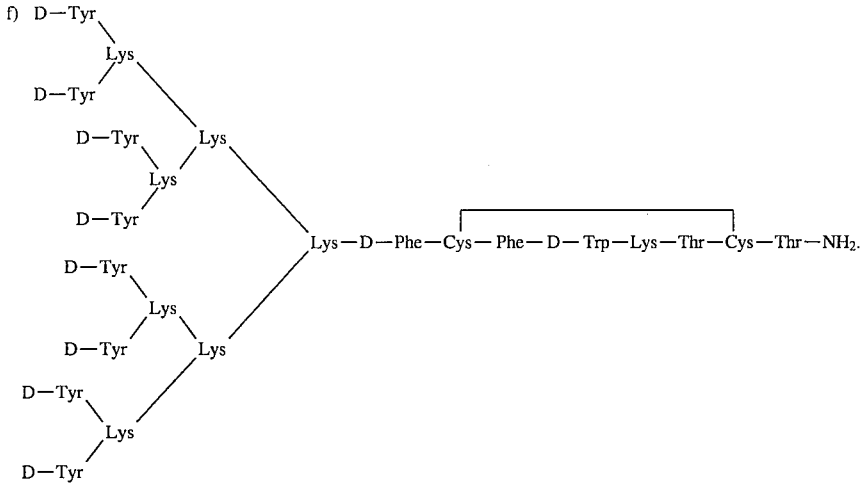

The compounds of the invention can be admixed with a pharmaceutically acceptable carrier to make a pharmaceutical composition.

The compounds of the invention can be used to detect in vivo a tumor expressing a somatostatin receptor by: 1) administering to a patient an amount of a radiolabeled compound of the invention effective to bind somatostatin receptors on cancerous cells in the patient, and 2) detecting radiation emitted by the radiolabeled compound bound to the cancerous cells.

The compounds of the invention can also be used to diagnose a condition associated with aberrant expression of a somatostatin receptor and the production of a biochemical marker (e.g., cancers such as gastrinoma), by:

a) administering to a patient an amount of a compound of the invention effective to inhibit production of a biochemical marker associated with said condition; and 2) determining a level of the biochemical marker produced after administration of the compound relative to a level of the biochemical marker produced prior to administration of the compound; a decrease in the level of the biochemical marker (relative to the level of biochemical marker prior to administration of the compound) is indicative of a condition associated with aberrant expression of a somatostatin receptor and/or is controllable by administration of somatostatin or somatostatin analog.

The compounds of the invention can also be used to treat a patient having a condition associated with aberrant expression of a somatostatin receptor (e.g., cancer), by administering to the patient an amount of a compound of the invention effective to bind somatostatin receptors of cells aberrantly expressing said receptors.

The compounds of the invention can also be used to treat a patient having a condition associated with aberrantly increased production of a factor(s) regulatable by somatostatin by administering to the patient a therapeutically effective amount of a compound of the invention (e.g., acromegaly).

The compounds of the invention are also useful for diagnosing in vitro a tumor associated with aberrant expression of a somatostatin receptor by: a) obtaining from a patient a sample of tissue suspected of aberrantly expressing a somatostatin receptor; b) contacting the sample with a detectably labeled compound of the invention to allow binding of the compound to somatostatin receptors of the sample; and c) measuring binding of the label to the sample. A level of label binding to the sample significantly greater than (e.g., more than twice) a level of label binding to a negative control sample is indicative of a tumor associated with aberrant expression of a somatostatin receptor in said patient.

In one aspect the invention features a method for detecting in situ a tumor expressing a somatostatin receptor which involves: 1) administering to a patient an amount of a radiolabeled compound of the invention effective to bind somatostatin receptors on cancerous cells in the patient, and 2) detecting radiation emitted by the radiolabeled compound bound to the cancerous cells.

In another aspect, the invention features a method for diagnosing a condition associated with aberrant expression of a somatostatin receptor and the production of a biochemical marker (e.g., cancers such as neuroendocrine tumors and gastrinomas, and conditions such as acromegaly). This diagnostic method involves: a) administering to a patient an amount of a compound of the invention effective to inhibit production of a biochemical marker associated with said condition; and 2) determining a level of the biochemical marker produced after administration of the compound relative to a level of the biochemical marker produced prior to administration of the compound. A decrease in the level of the biochemical marker (relative to the level of biochemical marker prior to administration of the compound) is indicative of a condition associated with aberrant expression of a somatostatin receptor.

In another aspect, the invention features a method for diagnosing in vitro a tumor associated with aberrant expression of a somatostatin receptor, which involves: a) obtaining from a patient a sample of tissue suspected of aberrantly expressing a somatostatin receptor; b) contacting the sample with a detectably labeled compound according to the invention to allow binding of the compound to somatostatin receptors of the sample; and c) detecting a level of binding of the label to the sample. A level of binding of the label to the sample significantly greater than a level of binding to a negative control sample is indicative of a tumor associated with aberrant expression of a somatostatin receptor in said patient.

As used herein, "somatostatin analog" or "somatostatin peptide analog" means a structural derivative of native somatostatin and which binds a somatostatin receptor with at least about 5% of the avidity and/or affinity of native somatostatin. Analogs include both somatostatin antagonists and agonists. In general, somatostatin peptide analogs: 1) contain the amino acid sequence Cys-$X_1$-D-Trp-Lys-$X_2$-

Cys-Thr, or a D-amino acid substituted (i.e., any of the amino acids can be D- rather than L-) derivative thereof, wherein $X_1$ is preferably Phe or Tyr, and $X_2$ is preferably Thr or Val; and 2) range from about 1,000 Da to 15,000 Da in molecular weight.

As used herein, by "halogen" or "halogen atom" means fluorine, chlorine, bromine, iodine, or astatine.

As used herein, "aberrant expression of a somatostatin receptor" means somatostatin receptor expression on the surface of a specific normal cell type, at a level significantly greater than a surface expression level normally associated with that specific normal cell type. For example, tumors characterized as neuroblastomas aberrantly express somatostatin receptors in that the cells of a neuroblastoma have a higher level of somatostatin receptor surface expression than the nerve tissue from which the neuroblastoma was derived. Aberrant cell surface expression can occur through a variety of mechanisms such as up-regulation of transcription and translation of nucleic acid encoding somatostatin receptors, up-regulation of surface presentation, and/or down-regulation of receptor degradation and/or increased internalization.

As used herein, "biochemical marker" means a hormone, peptide, protein, or other biological substance associated with a specific biological phenomenon (e.g., cell proliferation, cell motility, tumor metastasis) or cell type (e.g., neuroendocrine cell, endocrine cell, tumor cell).

As used herein, "a condition associated with aberrantly increased production of a factor regulatable by somatostatin" means a condition characterized by production of a somatostatin regulatable factor(s) which production is significantly greater than production of that same factor in the absence of the condition. Acromegaly, which is associated with over production of the somatostatin-regulatable factor, growth hormone and insulin-like growth factor-1, is an example of such a condition.

As used herein, "factor regulatable by somatostatin" means any hormone, peptide, protein, or other biological substance which is decreased or inhibited in its expression and/or secretion in the presence of somatostatin. Examples of somatostatin-regulatable factors include, but are not limited to, growth hormone, adrenocorticotropin hormone (ACTH), prolactin, thyroid stimulating hormone, insulin, glucagon, motilin, gastric inhibitory peptide (GIP), vasoactive intestinal peptide (VIP), secretin, cholecystokinin (CCK), bombesin, thyroid releasing hormone (TRH), aldosterone, cytokines (e.g., interleukins, interferons), growth factors (e.g., epidermal growth factor (EGF), nerve growth factor (NGF)), gastrin, and gastrin releasing peptide (GRP).

As used herein, "pharmaceutical composition" means a composition appropriate for administration to a patient for use in a method of diagnosis or treatment.

As used herein, "therapeutically effective amount" means an amount of a composition effective in the treatment of a condition associated with aberrantly increased production of a factor regulatable by somatostatin or aberrant expression of a somatostatin receptor, particularly a tumor having receptors which can be bound by the multi-tyrosinated peptide administered.

One advantage of the invention is that multiple radioisotopic atoms can be bound to a single multi-tyrosinated somatostatin analog (i.e., a compound of the invention). Upon binding of a somatostatin receptor, these multi-labeled analogs deliver a plurality of radioisotopes (of the same or different elements and/or of the same or different energy levels) to a single receptor, thus providing a more potent radiation dose to the site for therapy and a stronger radioactive signal for diagnostic radiolocalization techniques having increased sensitivity.

Another advantage of the invention is that multi-tyrosinated somatostatin analogs have increased half-lives in vivo relative to conventional somatostatin analogs, are resistant to enzymatic degradation, and have increased blood-brain barrier penetration.

Another advantage of the invention is that halogenated multi-tyrosinated somatostatin analogs irreversibly bind somatostatin receptors, thus allowing detection of bound analog over a longer time period relative to reversibly-binding analogs.

Other features and advantages of the invention will be apparent from the following description of the preferred embodiments thereof, and from the claims.

DETAILED DESCRIPTION

Figure 1A:
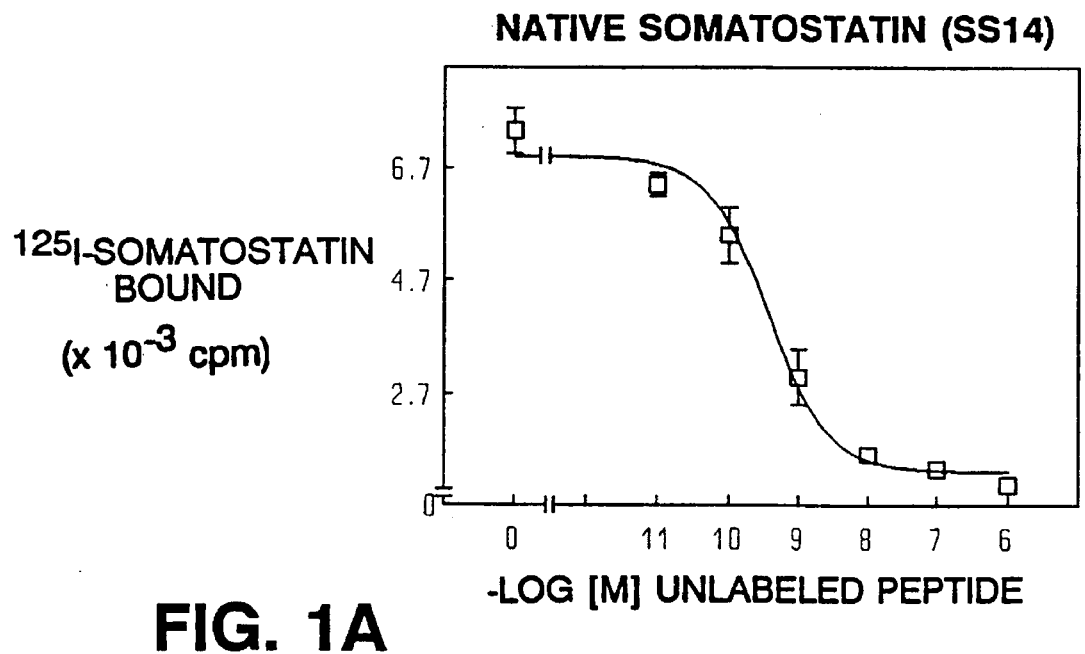
FIGS. 1A–D are graphs showing the somatostatin receptor binding curves for native somatostatin (FIG. 1A), WOC-2A (FIG. 1B), and WOC-3B (FIG. 1C), as well as a composite curve (FIG. 1D) showing the relative binding affinities of native somatostatin (open squares), WOC-2A (closed circles), WOC-3B (open diamonds), and lanreotide (open triangles).
Figure 1B:
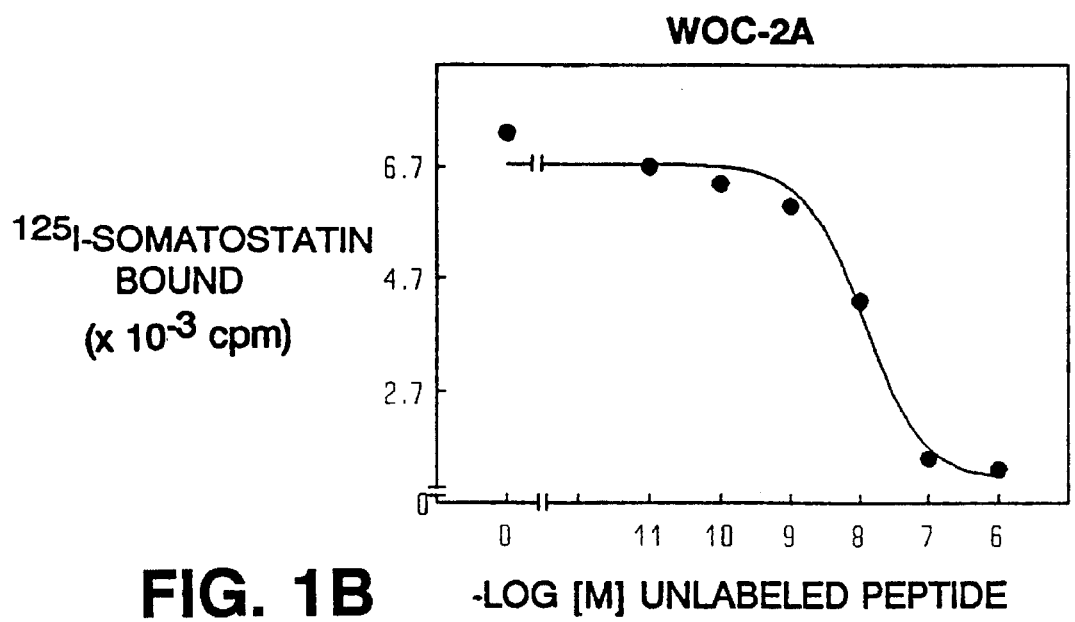
Figure 1C:
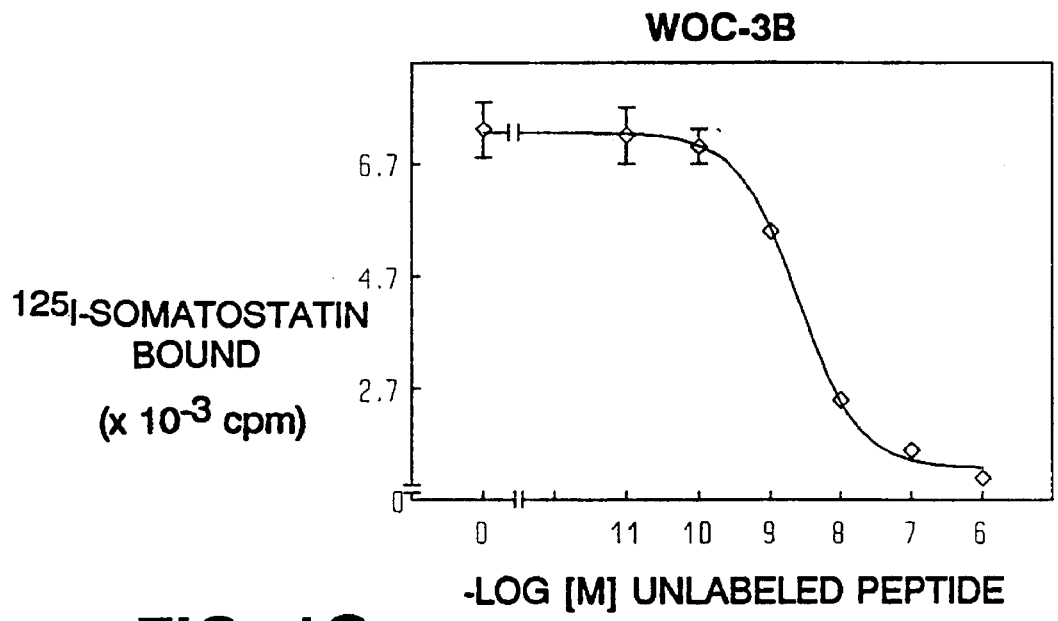
Figure 1D:
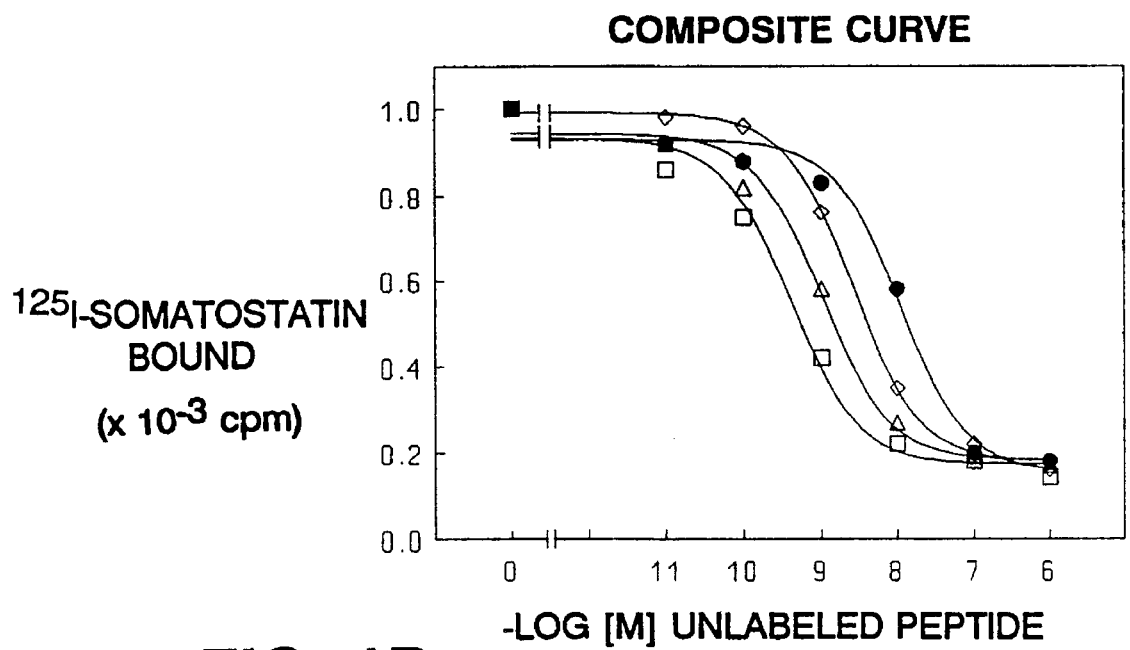

Multi-tyrosinated somatostatin analogs of the invention bind to somatostatin receptors with substantially the same affinity as native somatostatin. The multi-tyrosinated somatostatin analogs can be modified by halogenation of the tyrosine residues of the compound. Such halogenated analogs of the invention bind somatostatin receptors with such high affinity that the binding is nearly irreversible under physiological conditions. The multi-tyrosinated analogs of the invention can be further modified by detectable labeling, e.g. by binding a radioisotope (e.g., $^{125}I$, $^{127}I$, $^{123}I$, $^{129}I$, $^{131}I$) to the tyrosine residues and/or binding of other compounds (e.g., a fluorochrome such as a fluorescein) to a lysine residue of the analog, particularly an analog having a branched N-terminal extension containing lysines.

The multi-tyrosinated somatostatin analogs and halogenated derivatives thereof can be used in a variety of diagnostic and therapeutic methods. Exemplary uses of the analogs of the invention are briefly summarized below.

Summary of diagnostic and therapeutic methods of the invention

I. Diagnosis and treatment of conditions associated with aberrant somatostatin receptor expression and production of a biochemical marker The multi-tyrosinated somatostatin analogs can be used to diagnose conditions associated with aberrant expression of a somatostatin receptor and concomitant production of a biochemical marker. If administration of the multi-tyrosinated analog results in a decrease in biochemical marker levels relative to the biochemical marker level prior to analog administration, then the patient has a condition associated with aberrant expression of a somatostatin receptor. The multi-tyrosinated analog can be unmodified or modified by halogenation. Preferably, the analog is halogenated and non-radioactive.

Multi-tyrosinated somatostatin analogs and halogenated derivatives thereof can also be used to treat patients having a condition associated with aberrant expression of a somatostatin receptor and/or aberrantly increased production of a factor(s) regulatable by somatostatin. The analog administered in this therapeutic method can be modified or unmodified. Preferably the analog is halogenated and non-radioactive.

II. Diagnosis and treatment of somatostatin receptor-expressing tumors

Radiolabeled derivatives of the multi-tyrosinated somatostatin analogs of the invention can be used in the detection and diagnosis of tumors which express somatostatin receptors. These diagnostic methods can be performed: 1) in vivo; 2) in situ; or 3) in vitro.

The in vivo diagnostic methods involve administration of radiolabeled multi-tyrosinated analog, preferably a $^{123}$I- or $^{131}$I-radiolabeled analog, and detection of the somatostatin receptor-expressing tissue by in vivo imaging techniques known in the art (e.g., nuclear medicine scintigraphic methods).

The in situ diagnostic methods involve administration of radiolabeled multi-tyrosinated analog, preferably a $^{125}$I-radiolabeled analog immediately prior to, or during, surgical removal of the tumor. The tissue expressing somatostatin receptors is detected directly in the patient during surgery, and tissue having a significant amount of bound radiolabel is excised.

The in vitro diagnostic method is performed on, for example, a tissue biopsy sample by contacting the sample with detectably labeled multi-tyrosinated analog.

In general, binding of the analog to a tissue at a level greater than negative control levels (e.g., levels of analog binding to normal tissue (in vivo) or a saturated normal tissue sample (in vitro) is indicative of a tumor associated with aberrant expression of a somatostatin receptor. Patients having somatostatin receptor-expressing tumors, as determined by the methods described above or by conventional diagnostic methods, can be treated using a radiolabeled multi-tyrosinated somatostatin analog, preferably a $^{131}$I-radiolabeled analog, of the invention.

Each of these uses for multi-tyrosinated somatostatin analogs are described in detail below. A general description of the synthesis and modification of the analogs of the invention will be first described.

Synthesis of multi-tyrosinated somatostatin analogs

The formula of the multi-tyrosinated somatostatin analogs of the invention can be based upon the amino acid sequence, or a derivative of the amino acid sequence, of any of a variety of commercially available somatostatin peptide analogs or other somatostatin peptide analogs known in the art (see, for example, the somatostatin analogs described in PCT Application WO 91/09056 (1991); PCT Application WO 91/0114 (1991); EP Published Application No. 0 505 680 A1 (1992); EP Published Application No. 0 363 589 A2 (1990); EP Application No. 0 203 031 A2 (1986); EP Published Application No. 0588754A1; U.S. Pat. No. 4,904,642 (1990); U.S. Pat. No. 4,871,717 (1989); U.S. Pat. No. 4,853,371 (1989); U.S. Pat. No. 4,725,577 (1988); U.S. Pat. No. 4,684,620 (1987); U.S. Pat. No. 4,650,787 (1987); U.S. Pat. No. 4,603,120 (1986); U.S. Pat. No. 4,585,755 (1986); U.S. Pat. No. 4,522,813 (1985); U.S. Pat. No. 4,486,415 (1984); U.S. Pat. No. 4,485,101 (1984); U.S. Pat. No. 4,435,385 (1984); U.S. Pat. No. 4,395,403 (1983); U.S. Pat. No. 4,369,179 (1983); U.S. Pat. No. 4,360,516 (1982); U.S. Pat. No. 4,358,439 (1982); U.S. Pat. No. 4,328,214 (1982); U.S. Pat. No. 4,316,890 (1982); U.S. Pat. No. 4,310,518 (1982); U.S. Pat. No. 4,291,022 (1981); U.S. Pat. No. 4,238,481 (1980); U.S. Pat. No. 4,235,886 (1980); U.S. Pat. No. 4,224,190 (1980); U.S. Pat. No. 4,211,693 (1980); U.S. Pat. No. 4,190,648 (1980); U.S. Pat. No. 4,146,612 (1979); U.S. Pat. No. 4,133,782 (1979); Van Binst et al., *Peptide Res.*, 5:8 (1992); Prevost et al., *Cancer Res.*, 52:893 (1992); and Bachem California 1993–1994 Catalog 94–95 (1993), each of which are incorporated herein by reference.)

The compositions of the invention are generated by N-terminally extending somatostatin peptide analogs such as those exemplified above. The N-terminal extension can be either a linear, symmetrically branched, or asymmetrically branched peptide extension. Although the total number of tyrosine residues in the N-terminal extension can vary, it contains at least two tyrosine residues, preferably at least three tyrosine residues, more preferably at least four tyrosine residues, even more preferably at least eight tyrosine residues, and can contain up to 32 tyrosine residues or more.

N-terminally extended, multi-tyrosinated somatostatin analogs of the invention are of the general formula:

a) $(Y)_{n+1}P$,
b) $(Y)_n$—Ala—Y—P, or c) 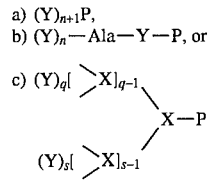

where a) P is a somatostatin peptide analog which binds to a somatostatin receptor; b) Y is D-tyrosine, L-tyrosine, or desamino-tyrosine; c) n is an integer from 1 to 32, inclusive, preferably 1 to 16, inclusive, more preferably 1 to 3, inclusive; d) each q, independently, is an integer from 1 to 32, inclusive, preferably 1 to 16, inclusive, more preferably 1 to 4, inclusive; and e) each s, independently, is an integer from 1 to 32, inclusive, preferably 1 to 16, inclusive, more preferably 1 to 4, inclusive; where q and s can be the same or different; and f) X is of the formula D—NH$_2$—CH(CH$_2$)$_m$NH$_2$—CO$_2$H or L—NH$_2$—CH(CH$_2$)$_m$NH$_2$—CO$_2$H, wherein m is an integer from 1 to 10, inclusive.

Preferably, the somatostatin analog "P" in the formula described above is of the formula:

a) Cys-Tyr-D-Trp-Lys-Val-Cys-Thr-NH$_2$ (a derivative of LANREOTIDE™);

b) Cys-Phe-D-Trp-Lys-Thr-Cys-Thr-NH$_2$ (a derivative of octreotide acetate); or c) Cys-Tyr-D-Trp-Lys-Thr-Cys-Thr(ol) (a derivative of octreotide acetate).

The ability of the multi-tyrosinated somatostatin analogs to bind somatostatin receptors and act as somatostatin receptor agonists or antagonists can be assessed in vitro using methods well known in the art (see, for example, O'Dorisio, M. S. et al., *Cell Growth and Differentiation*, 5:1–8, 1994). The activities of the analogs in such in vitro assays are predictive of the activities of the analogs in vivo.

Modification of multi-tyrosinated somatostatin analogs

The multi-tyrosinated somatostatin analogs can be modified by covalent binding of a non-radioactive halogen atom (e.g., fluorine, chlorine, bromine, iodine, or astatine), a fluorochrome, or a radioisotope (preferably a radioisotope of halogen) to a tyrosine residue of the analog's N-terminal extension.

Where the multi-tyrosinated somatostatin analog is modified by binding of a non-radioactive halogen atom to a tyrosine residue of the N-terminal extension, the halogen is preferably iodine. Halogenated analogs of the invention contain a halogen covalently bound to at least one tyrosine residue and preferably to multiple tyrosine residues in each molecule. Preferably about one-half, more preferably about three-fourths, most preferably all of the tyrosine residues in the N-terminal extension of the analog are bound to a radioactive or non-radioactive halogen atom. Multi-halogenated analogs of the invention can have prolonged half-lives relative to unmodified somatostatin analogs. Multi-halogenated analogs can also have enhanced blood-brain barrier penetration relative to unmodified somatostatin analogs. Halogenation increases the molecule's lipophilicity, which in turn enhances blood-brain barrier penetration (Banks et al., *Brain Res.* Bull, 15:287–292 (1985)). Methods for halogenating peptides are well known in the art (see, for example, Parker, *Radioimmunoassay of Biologically Active Compounds*, Prentice Hall, (1976), Chapter 5).

The multi-tyrosinated somatostatin analogs of the invention can be detectably labeled by binding a fluorochrome to an amine residue of the analog. For example, the fluorochrome (e.g., fluorescein isothiocyanate) can be specifically bound to lysine residues of the analog. Multi-fluorescinated somatostatin analogs, particularly multi-tyrosinated analogs having multiple lysines (e.g., in a branched N-terminal extension) are useful in detecting surface expression of somatostatin receptors in a variety of diagnostic and research reagent applications. For example, where the multi-fluorescinated analog is incubated with a mixed population of cells, and a cell subpopulation of somatostatin receptor-expressing cells isolated by FACS (fluorescent-activated cell sorting) using methods well known in the art.

Radioisotopes for radiolabeling the multi-tyrosinated somatostatin analogs of the invention include any radioisotope that can be covalently bound to a tyrosine residue of the analog. The radioisotopes can be selected from radioisotopes which emit either beta or gamma radiation, preferably gamma radiation. In addition, or alternatively, the multityrosinated somatostatin analogs can be modified to contain chelating groups that, for example, can be covalently bonded to lysine residue(s) of the analog. The chelating groups can then be modified to contain any of a variety of radioisotopes, such as gallium, indium, technetium, ytterbium, rhenium, or thallium (e.g., I, $^{67}$Ga $^{111}$In, $^{99}$mTc, $^{169}$Yb, $^{186}$Re).

Where the multi-tyrosinated somatostatin analog is modified by attachment of a radioisotope, preferable radioisotopes are those having a radioactive half-life corresponding to, or longer than, the biological half-life of the analog used. More preferably, the radioisotope is a radioisotope of a halogen atom (e.g., a radioisotope of fluorine, chlorine, bromine, iodine, and astatine), more preferably a radioisotope of iodine, even more preferably $^{123}$I, $^{124}$I, $^{125}$I, $^{129}$I, or $^{131}$I. Preferably the radioisotope has a half-life of from 1 hour to 60 days, preferably from 5 hours to 10 days, more preferably from 12 hours to 8 days.

The specific analog and radiolabel is selected according to the diagnostic or therapeutic method used, whether the diagnostic method is performed in vivo, in situ, or in vitro, the suspected location of the tumor (e.g., liver, lung, pancreas, brain), the metabolism of the analog selected, and the method used to detect bound radiolabeled analog. For example, where the diagnostic method is performed in situ (i.e., the radiolabel is detected directly in the patient's tissues during surgery), lower level energy isotopes are preferred, especially those isotopes emitting beta or gamma photons at energy levels less than about 300 kev, preferably less than abut 150 kev, more preferably less than 50 kev. The preferred radiolabel for in situ diagnosis is $^{125}$I. If the radiolabel is detected by nuclear medicine scintigraphy (i.e., nuclear medicine scanning), $^{123}$I is a preferred radiolabel. Where the analog is to be used as a therapeutic (e.g., in radiotherapy), $^{129}$I and $^{131}$I are preferred radiolabels.

Radiolabeled analogs of the invention will have at least one tyrosine having a covalently bound radioisotope. Where the multi-tyrosinated somatostatin analog contains multiple tyrosine residues, the analog can be radiolabeled such that about one-third of the tyrosine residues, preferably about one-half, more preferably about three-fourths, most preferably all of the tyrosine residues in the N-terminal extension of the analog are bound to the radioisotope. Radiolabeled multi-tyrosinated somatostatin analogs can contain multiple radioisotopes bound to a single analog, e.g., by binding of radioisotopes to multiple tyrosine residues and/or binding of up to two halogen radioisotopes per tyrosine residue, thus delivering multiple radioisotope atoms to a single somatostatin receptor. Because mono-halogenated tyrosine is generally more stable than di-halogenated tyrosine, multi-tyrosinated somatostatin analogs that contain mono-halogenated tyrosine residues are preferred. Analogs having 1) multiple tyrosine residues and 2) up to two halogen radioisotopic atoms bound to each tyrosine provide a high signal-to-noise ratio for use in detection methods, as well as a potent radiotherapeutic agents for cancer therapies. Methods for radiolabeling peptides are well known in the art.

Pharmaceutical compositions containing multi-tyrosinated somatostatin analogs

Pharmaceutical compositions containing a multi-tyrosinated analog suitable for use in the diagnostic and therapeutic methods of the invention are prepared according to methods well known in the art. In general, the pharmaceutical compositions are injectable formulations containing at least one multi-tyrosinated somatostatin analog and a pharmaceutically acceptable carrier. The pharmaceutically acceptable carrier can be any carrier known in the art, and is selected according to such factors as the route of administration, the diagnostic or therapeutic method used, and the analog to be administered.

In general, the concentration of multi-tyrosinated analog in the pharmaceutical composition is sufficient to deliver in a single dose an amount of the analog effective to bind to somatostatin receptors on the targeted tissue. Specific dosages and will vary according to several factors including the diagnostic or therapeutic method used, the multi-tyrosinated analog used (e.g., specific activity, somatostatin receptor binding affinity and avidity, molecular weight, number of radioisotopic atoms bound to the analog), the route of administration, the condition to be treated, and patient-specific variables such as age, weight, and severity of disease. For example, the routes of excretion of radiolabeled analogs affect efficacy in localizing small tumors, especially in the upper abdomen. In general analogs radiolabeled with $^{123}$I, $^{125}$I, or $^{131}$I are excreted primarily through the biliary tract and, subsequently, the gut.

Guidance for dosages appropriate for the specific diagnostic and therapeutic methods of the invention is provided in the description of each method provided below. Specific dosages of multi-tyrosinated analogs can be based upon dosages for conventional somatostatin analogs such as LANREOTIDE™ and octreotide acetate (see, for example, EP 0 588 754, published Mar. 23, 1994). Where the analog is to be administered to mimic wild-type somatostatin levels, the analog is administered to achieve circulating levels of picograms to nanograms. Dosage amounts for multi-tyrosinated somatostatin analogs are generally lower than those required for conventional somatostatin analogs due to the ability to bind multiple halogen atoms and radioisotopes to the N-terminal extension of the multi-tyrosinated analogs, the relative affinity and/or avidity of the multi-tyrosinated analogs for somatostatin receptors, and/or the enhanced half-life of multi-tyrosinated analogs.

The pharmaceutical compositions of the invention can contain compounds in addition to the multi-tyrosinated analogs. For example, the pharmaceutical composition can contain compounds to provide relief of symptoms associated with the condition to be treated (e.g., pain-relieving compounds, anti-inflammatories, etc.). Where the multi-tyrosinated analog is radiolabeled, the pharmaceutical composition can additionally contain compounds to increase analog stability, e.g., by inhibiting autoradiolysis. Such compounds include free radical scavengers such as ascorbic acid, benzoic acid, 2,5-dihydroxybenzoic acid. Autoradiolysis can also be prevented by dilution, i.e., storage of the radiolabeled analogs at lower concentrations.

Conditions amenable to diagnosis using multi-tyrosinated somatostatin analogs

The multi-tyrosinated somatostatin analogs of the invention can be used in the diagnosis of conditions associated with conditions associated with aberrant expression of a somatostatin receptor and/or aberrant production of a somatostatin-regulatable factor. These two general classes of conditions are not exclusive one from another. For example, various endocrine cancers are associated with aberrant production of somatostatin-regulatable factors and with aberrant somatostatin receptor expression. Conversely, aberrant production of a somatostatin regulatable factor does not necessarily accompany all conditions associated with aberrant somatostatin receptor expression.

Conditions associated with aberrantly increased production of a factor regulatable by somatostatin include any condition characterized by production of a somatostatin regulatable factor which is significantly greater than production of that same factor in the absence of the condition. Examples of such conditions include cancer, acromegaly, and sarcoidosis. Somatostatin regulatable factors include any hormone, peptide, protein, or other biological product which is decreased or inhibited in its expression and/or secretion in the presence of somatostatin. Examples of somatostatin-regulatable factors include growth hormone, adrenocorticotropin hormone (ACTH), prolactin, thyroid stimulating hormone, insulin, glucagon, motilin, gastric inhibitory peptide (GIP), vasoactive intestinal peptide (VIP), secretin, cholecystokinin (CCK), bombesin, thyroid releasing hormone (TRH), aldosterone, cytokines (e.g., interleukins, interferons), growth factors (e.g., epidermal growth factor, neuronal growth factor), gastrin, pancreatic polypeptide (PP), and gastrin releasing peptide (GRP).

Conditions associated with aberrant expression of a somatostatin receptor are also amenable to diagnosis and therapy using the multi-tyrosinated somatostatin analogs of the invention. Conditions associated with aberrant expression of a somatostatin receptor include any condition where a specific cell type expresses a somatostatin receptor at a level significantly greater than an expression level normally associated with that specific cell type. Exemplary conditions which aberrantly express somatostatin receptors include various types of solid or non-solid tumors and endocrine tumors. Examples of tumors that can be diagnosed and treated according to the invention include pituitary tumors; central nervous system tumors; brain tumors; breast tumors; ovarian tumors; prostate tumors; kidney tumors; gastrointestinal tract tumors (colonic; pancreatic, stomach); lung tumors (e.g., bronchioloalveolar carcinoma, small cell carcinoma); myelomas; lymphomas (e.g., non-Hodgkins lymphoma and Hodgkins lymphoma); neuroendocrine tumors (e.g., carcinoid, VIPoma, insulinoma, glucagonoma, medullary thyroid carcinoma, gastrinoma, pheochromocytoma, pituitary tumors); nervous system tumors (e.g., neuroblastoma, glioma, medulloblastoma, paraganglioma, primitive neuroectodermal tumors, meningioma, astrocytoma); bone tumors (e.g., osteogenic sarcoma, Ewing's sarcoma); and metastases thereof. Additional somatostatin receptor-expressing tumors are described by Krenning et al., *Europ. Nuc. Med.*, 20:716–731, 1993. The diagnostic methods of the invention can thus be used to identify any primary, multicentric, or metastatic tumor which expresses a somatostatin receptor.

In general, the multi-tyrosinated somatostatin analog is selected according to a variety of factors such as the diagnostic method used, the ability of the analog to accumulate in a targeted, defined cell population, e.g., a specific affected cell type(s), tissue(s), or organ(s), the half-life of the analog, and the analog's binding affinity and/or avidity to a somatostatin receptor.

The diagnostic methods of the invention can be used to identify a primary, somatostatin receptor-expressing tumor; to identify metastases of such tumors; as a screen for relapse (i.e., renewed tumor growth) in a patient; or as a routine screen for somatostatin receptor-expressing tumors in a patient susceptible to tumor development.

Diagnosis of conditions associated with aberrant production of a somatostatin-regulatable factor and/or aberrant expression of a somatostatin receptor The multi-tyrosinated somatostatin analogs of the invention can be administered to a patient to determine whether the patient has a condition associated with aberrant production of a somatostatin-regulatable factor and/or aberrant expression of a somatostatin receptor. In general, these conditions are diagnosed by examining the effect of administration of an unlabeled (i.e., non-radioactive) multi-tyrosinated somatostatin analog upon the amount of a biochemical marker.

The analog administered for diagnosis is preferably a non-radioactive multi-tyrosinated somatostatin analog, more preferably a non-radioactive halogenated multi-tyrosinated somatostatin analog. The amount of analog administered can vary according to a variety of factors including the biological activity and half-life of the analog selected, the type and suspected location of the tumor, and patient dependent variables including size, weight, and tumor load. The specific amount administered is generally from about 0.1 pg to 1,000 μg, preferably about 1 ng to 500 μg, more preferably about 1 μg to 200 μg, normally about 100 μg. The amount administered will increase with increasing molecular weight of the multi-tyrosinated analog administered.

The biochemical marker can be any hormone, peptide, protein, or other biological product associated with a specific cell type (e.g., endocrine cell, tumor cell) or biological phenomenon (e.g., cell proliferation, cell motility, tumor metastasis). The biochemical marker can be present in any body fluid of the patient, preferably urine or blood. The sensitivity of the diagnostic method can be increased by determining the levels of two or more biochemical markers (e.g., gastrin and VIP). Detection of a biochemical marker that is not regulated by somatostatin can serve as a negative control. A significant decrease in the amount of the biochemical marker after administration of the multi-tyrosinated analog indicates that the condition is associated with production of a somatostatin-regulatable factor and/or expression of a somatostatin receptor. Preferably, the decrease in the biochemical marker is at least about a 20% decrease, more preferably about 30%, even more preferably about 50%. Reduction of biochemical marker levels in response to multi-tyrosinated somatostatin analog administration indicates that, for example, the analogs will bind to the tumor cell surfaces for preoperative or intraoperative detection and/or the analogs will be efficacious in treatment of the condition, (e.g., biochemical marker production is controllable by somatostatin or somatostatin analog administration).

For example, a blood sample (control sample) is obtained from a patient having a gastrinoma and the amount of gastrin determined using methods well known in the art. An injectable formulation containing about 100 µg to 200 µg of a multi-tyrosinated somatostatin analog is administered to the patient. The analog can be administered by parenteral injection, preferably by intravenous injection. A second blood sample is obtained from the patient as early as 30 sec after analog administration, usually about 10 min after administration, up to about 30 min to 1 hr after administration, normally no more than 2 hrs after administration. The biochemical marker can be detected until analog blood levels are zero and the affected cell has recovered (normally about 30 to 60 min). The amount of gastrin in the blood sample is determined and compared to the amount of gastrin in the control sample. If the amount of gastrin in the sample obtained after analog administration is significantly less than the amount of gastrin in the control sample, then the gastrinoma expresses somatostatin receptors and is amenable to the preoperative and intraoperative tumor localization methods, as well as the therapeutic methods, of the invention.

In another example, a control blood sample is obtained from a patient suspected of having acromegaly. The amount of growth hormone (GH) and/or insulin-like growth factor-1 (IGF-1) present in the control sample is determined according to methods well known in the art. About 100 µg of a multi-tyrosinated somatostatin analog is administered by intravenous injection to the patient and a second blood sample obtained about 30 min after administration. The amount of GH and/or IGF-1 in the second blood sample is determined and compared to the amount of GH and/or IGF-1 in the control sample. If the amount of GH and/or IGF-1 in the second sample is significantly lower than the amount of GH and/or IGF-1 in the control sample, then the patient's condition is amenable to treatment with multi-tyrosinated somatostatin analogs.

Preoperative diagnosis of tumors aberrantly expressing somatostatin receptors

Radiolabeled multi-tyrosinated peptide analogs can be used in a method for preoperative detection and localization of a tumor expressing a somatostatin receptor. Tumors amenable to detection using the radiolabeled analogs of the invention can be identified by determining if the tumor produces a somatostatin-regulatable factor as described above. Pre-screening patients using the diagnostic method described above can be more cost-effective since, for example, the diagnostic method described above does not require that the analog be radiolabeled, and generally requires lower analog dosages than tumor localization methods. However, such pre-screening assays are not required for any of the pre-operative, intraoperative, or post-operative diagnostic methods of the invention. Furthermore, not all somatostatin receptor-expressing tumors produce a somatostatin-regulatable factor, or the identity of the somatostatin-regulatable factor may be unknown. Therefore, it may be desirable to perform the pre-operative tumor localization method of the invention even when diagnostic methods to detect production of somatostatin-regulatable factors provides negative results. Binding of a multi-tyrosinated analog is sufficient to identify tumors that express somatostatin receptors.

In general, preoperative diagnosis is accomplished by administering a radiolabeled multi-tyrosinated somatostatin analog, preferably a radiolabeled, halogenated multi-tyrosinated somatostatin analog, to the patient by parenteral injection, preferably by intravenous injection. Selection of the specific multi-tyrosinated analog and the specific radiolabel will vary according to a variety of factors including the type and location of the tumor to be detected, and the radiolabel detection technique used. Preferably the radiolabel is a gamma-emitting radioisotope, more preferably a radioisotope of iodine, even more preferably $^{123}$I.

The appropriate dosage of the labeled multi-tyrosinated somatostatin analogs will vary according to a variety of factors including the label and the multi-tyrosinated somatostatin analog used, the type and location of tumor to be imaged, and various patient-dependent factors such as the patient's age and weight, and the extent of disease (e.g., size and number of tumors). A suitable dose for injection is an amount effective to enable imaging by nuclear medicine scintigraphy procedures known in the art (e.g., computerized tomography (CT), positron emission tomography (PET), or single photon emission computerized tomography (SPECT)). Where the analog is radiolabeled with a gamma-emitting radioisotope, analog binding is normally detected by SPECT. For example, the amount of radioactivity administered in a single dose can have an activity of about 10 µCi to 50 mCi, preferably about 100 µCi to 25 mCi, more preferably about 500 µCi to 20 mCi, normally about 1 mCi to 10 mCi, usually about 10 mCi.

Following administration of the radiolabeled multi-tyrosinated somatostatin analog, the somatostatin receptor-expressing tumors can be detected as early as 1 min after administration, preferably about 60 min after administration, more preferably about 1 hr after administration, up to 12 hr to 96 hr, and as long as 2 to 3 weeks or more after administration.

In general, detection of somatostatin receptor-expressing tumors is performed after allowing a sufficient time for clearance of unbound or non-specifically bound radiolabeled multi-tyrosinated analog. Clearance of unbound and/or non-specifically bound analog decreases the radioactive signal associated with normal tissue, thus providing an increased signal-to-noise ratio (i.e., radiolabel bound to tumor tissue versus normal (background) tissue). Therefore, detection of bound, radiolabeled multi-tyrosinated analog is preferably performed several hours (e.g., 8 hrs to 24 hrs) to several days (e.g. 2 days to 7 days) after administration. In general, detection is performed 24 hrs to 48 hrs after administration. Moreover, due to the irreversible or nearly irreversible binding of halogenated, multi-tyrosinated somatostatin analogs, nuclear medicine scanning to detect somatostatin receptor-expressing tissue can be performed as a follow-up to surgery or therapy several weeks after initial analog administration without the need for administration of additional analog.

Tumors are visualized as tissue which binds the radiolabeled multi-tyrosinated analog at a level significantly higher than a level of binding of the radiolabeled analog by normal tissue. The tumor/normal tissue ratio of distribution of the radiolabeled analog will generally be about 2:1, preferably about 3:1, more preferably about 4:1, and can be up to 6:1 to 12:1 or higher.

The tumor can also be detected by the identification of tissue in which the radiolabeled analog accumulates over time. As discussed above, detection of radiolabeled analog binding is preferably performed after allowing clearance of unbound or non-specifically bound analogs from normal tissue. Tissue having higher levels of radiolabel associated at a later time point relative to an earlier time point (e.g., 36 hrs versus 12 hrs) is identified as somatostatin receptor expressing cancerous tissue. After the somatostatin receptor-expressing tumor has been identified, the tumor can be removed by surgery. Alternatively, or in addition, the patient can be treated by administration of unlabeled or radiolabeled multi-tyrosinated somatostatin analogs, or using conventional therapeutic methods.

Intraoperative (in situ) diagnosis of tumors aberrantly expressing somatostatin receptors Multi-tyrosinated somatostatin analogs can also be used to identify somatostatin receptor-expressing tumors during surgery. Intraoperative localization of tumors can be particularly useful in, for example, identification of tumor metastases undetected by conventional radiographic tumor localization techniques. Tumors amenable to intraoperative detection method of the invention can be identified by determining if the tumor produces a somatostatin-regulatable factor, by determining if the tumor binds a multi-tyrosinated analog using the diagnostic assay and preoperative imaging techniques as described above, or by using conventional diagnostic methods.

In general, intraoperative tumor detection is accomplished by administering a radiolabeled multi-tyrosinated somatostatin analog to the patient by parenteral injection, preferably by intravenous injection, and detection of bound radiolabel in situ. Where the general location of the tumor is known (e.g., preoperative diagnosis indicated that the tumor(s) was in a specific organ), the radiolabeled analog can be injected directly into the involved site. Tissue associated with aberrant expression of somatostatin receptors are identified as tissue having increased radiolabeled analog binding relative to radiolabeled analog binding to normal tissue. Binding of the radiolabeled analogs to the tumor can be detected as early as 1 min after injection and can continue to be monitored until the conclusion of surgery (normally 1 hr to 8 hrs after injection).

Selection of the specific multi-tyrosinated analog and the specific radiolabel will vary according to a variety of factors including the type and location of the tumor to be detected, and the radiolabel detection technique used. Preferably the radiolabel is a beta-emitting or gamma-emitting radioisotope, more preferably a gamma-emitting radioisotope, even more preferably a radioisotope of iodine, most preferably $^{125}$I. Lower level energy radioisotopes are preferred radiolabels, especially radioisotopes exhibiting photon emission energy levels less than about 300 kev, preferably less than about 150 kev.

The appropriate dosage of the radiolabeled multi-tyrosinated somatostatin analogs will vary according to several factors including the radiolabel and the multi-tyrosinated somatostatin analog used, the type and location of tumor to be detected, and various patient-dependent factors such as the extent of disease (e.g., size and number of tumors) or other concomitant medical conditions. A suitable dose for injection is an amount effective to bind the cancerous tissue and enable detection of the radiolabel using a hand-held probe. The specific amount of radiolabeled multi- tyrosinated somatostatin analog administered for intraoperative tumor detection is from about 10 µCi to 100 mCi, preferably from about 100 µCi to 50 mCi, more preferably from about 500 µCi to 40 mCi, usually from about 1 mCi to 10 mCi, normally less than 2 mCi. In general, about 0.01 mg to 100 mg, normally about 0.1 mg to 1.0 mg ($1\times10^5$–$1\times10^6$ cells) of radiolabeled tumor tissue per gram of total tissue produces a level of radiation sufficient to trigger the hand-held detector. The radiolabeled multi-tyrosinated analog can be administered during surgery, or as early as 30 min, normally as early as about 1 hr to 2 hrs before surgery.

As discussed in the preoperative diagnostic method described above, detection of bound analog is preferably performed after clearance of unbound or non-specifically bound analog. Thus, intraoperative detection is preferably performed several hours (e.g., 6 hrs to 24 hrs) up to several days (e.g., 2 days to 8 days) or weeks after administration. Moreover, where the somatostatin receptor-expressing tumor was identified using the preoperative diagnostic method described above, intraoperative diagnosis can be performed without administration of additional radiolabeled multi-tyrosinated analog.

Methods and devices for the detection of beta- and gamma-radiation are well known in the art. U.S. Pat. No. 5,008,546, incorporated herein by reference, describes a probe suitable for detection of beta-emitting radioisotopes. Suitable hand-held devices for detection of gamma-emitting radioisotopes are described in U.S. Pat. Nos. 4,801,803, 4,889,991, and 5,070,878, incorporated herein by reference. Additional radiation detection devices can be used as necessary. Radiation probes can be used as part of an endoscope, laparoscope, bronchoscope, or other specific instrument. During in situ detection, normal tissue which does not bind the radiolabeled multi-tyrosinated analog is used as a "reference" (negative control) tissue. Detection of gamma counts greater than a pre-selected number of counts (e.g., the square root of at least two standard deviations, preferably at least three standard deviations) over background (e.g., above the mean reference tissue counts) is indicative of a tissue which has bound the radiolabeled analog by virtue of having an increased number of somatostatin receptors. The radiolabeled tissue is then resected and the detection method continued until all detectable radiolabeled tissue is removed.

For example, where the patient has a gastrinoma 10 µCi to 1 mCi of $^{125}$I-multi-tyrosinated somatostatin analog is injected intravenously and gamma counts obtained in situ with a hand-held gamma detector. Gamma count detection is performed over the pancreas, stomach, duodenum, proximal, mid and distal small bowel, small bowel mesentery, colon, bladder, liver, kidneys, thyroid, heart and aorta. Subsequently the detector is switched to a scanning mode that allows "squelching" of background counts from an adjacent reference tissue. Gamma counts during a 1 second to 60 second period, normally about a 5 second period, are determined over a reference tissue and the control unit calculates both the average and the standard deviation of this signal. When the gamma detector is passed over tissue with gamma counts greater than the square root of three standard deviations above the mean reference tissue counts a "siren" is activated. The hand-held gamma detector can be used in the scan mode to identify single foci of increased counts for resection.

Postoperative (in vitro) diagnosis of tumors aberrantly expressing somatostatin receptors Diagnosis of tumors that aberrantly express somatostatin receptors can be determined by binding of detectably labeled multi-tyrosinated somatostatin analogs to a tissue sample in vitro. First, a sample of tissue is obtained from a patient suspected of having a tumor that aberrantly expresses a somatostatin receptor. The tissue sample can be prepared for incubation with the detectably labeled analog according to a variety of methods well known in the art. For example, the tissue can be separated into a single cell suspension and the single cells bound to a solid support (e.g., a well of a microliter plate). Alternatively, the cells in the tissue sample are lysed and a protein fraction primarily composed of cell surface membrane proteins prepared according to methods known in the art (O'Dorisio et al., *Cell Growth and Differentiation*, 5:1–8 (1994)).

The tissue sample is then incubated with a detectably labeled multi-tyrosinated somatostatin analog, preferably a halogenated multi-tyrosinated analog. A tissue sample which contains no somatostatin receptor can serve as a negative control. The detectable label can be any detectable label known in the art, preferably a fluorochrome or a radiolabel. Where the detectable label is a fluorochrome, fluorescein is the preferred label. Where the detectable label is a radiolabel, the detectable label is preferably a radioisotope of iodine, more preferably $^{125}$I. Competing, unlabeled, somatostatin receptor ligand is added to determine specific binding to receptors. The amount of unlabeled analog incubated with the samples is in increasing amounts up to levels in excess of that required to bind the somatostatin receptors in the control sample, preferably about 10-fold excess, more preferably about 100-fold excess. Incubation is carried out for a time sufficient to allow competitive binding of the labeled and unlabeled analogs to the somatostatin receptor in the samples.

After incubation, unbound material is removed from the sample by washing and the bound label detected. Where the detectable label is a radiolabel, detection can be accomplished with a scintillation counter. If the level of detectable label bound to the test sample is significantly higher than the level of detectable label bound to the negative sample, and the binding of labeled peptide is competitively inhibited by unlabeled peptide, then the tissue sample expresses a somatostatin receptor. The assay results indicate whether 1) the patient is amenable to diagnostic scanning, 2) the patient's tumor is amenable to treatment with the multi- tyrosinated somatostatin analogs of the invention, and 3) the patient's condition can be monitored using the preoperative methods described above.

Therapeutic administration of multi-tyrosinated somatostatin analoogs

Patients having a condition associated with aberrantly increased production of a somatostatin-regulatable factor and/or a condition associated with aberrant expression of a somatostatin receptor can be treated by administration of multi-tyrosinated somatostatin analogs. Patients having a condition amenable to treatment with the analogs of the invention can be identified using the diagnostic methods described above, although this is not a necessary prerequisite for the methods of treatment described herein. The method of treatment of the invention can be implemented as a primary therapy or as a follow-up therapy after surgery (e.g., after tumor resection).

Multi-tyrosinated somatostatin analogs for administration as therapeutic agents can be unlabeled, halogenated, fluorescinated, or radiolabeled. The selection of the specific analog is dependent upon the condition to be treated. For example, where the condition is associated only with aberrantly increased production of a somatostatin-regulatable factor (e.g., acromegaly, sarcoidosis), the analog is preferably an unlabeled multi-tyrosinated somatostatin analog, more preferably a halogenated multi-tyrosinated somatostatin analog. Where the patient has a condition associated with aberrant expression of a somatostatin receptor (e.g., a tumor), the analog is preferably a radiolabeled multi-tyrosinated somatostatin analog, more preferably a radiolabeled halogenated analog, even more preferably a $^{129}$I- or $^{131}$I-radiolabeled multi-tyrosinated somatostatin analog. Where a radiolabeled multi-tyrosinated analog is used, the peptide can be labeled just prior to administration, e.g., 24 hr or less before administration.

The multi-tyrosinated somatostatin analogs can be administered by any conventional route, preferably by parenteral injection in the form of an injectable solution or suspension. The multi-tyrosinated analogs can also be administered by infusion, e.g., an intravenous infusion of 30 min to 60 min. The multi-tyrosinated somatostatin analogs can be administered at or near the tumor site, e.g., using an angiographic intraarterial or intravenous regional catheter inserted into a vein or artery that feeds the tumor. The route of administration is selected according to the tumor site, the affinity and specificity of the analog, the half-life of the multi-tyrosinated analog, the half-life of a radiolabel bound to the analog, and other factors appreciated by one of ordinary skill in the art.

Dosages used in the therapeutic method of the invention will vary depending upon a variety of factors such as the specific condition to be treated, the radiolabel and multi-tyrosinated somatostatin analog used, and patient variables such as size, weight, and the severity of disease (e.g., tumor size and tumor load). The amount of multi-tyrosinated somatostatin analog for administration can be determined by calculating the amount of radiolabeled analog delivered to the target using the in vivo diagnostic method described above. Methods for calculating dosages using dosimetric techniques are routine and well known in the art (see, for example, Fisher et al., *Cancer*, 73:905–911, 1994). In general, the specific dosage delivered is from about 0.1 pg/kg to 500 µg/kg, preferably about 1 ng/kg to 250 µg/kg, normally about 200 ng/kg of multi-tyrosinated somatostatin analog. Where the analog is radiolabeled, the analog can be administered at a dosage range having a radioactivity of from about 0.1 µCi/kg to 50 mCi/kg body weight, preferably about 1 µCi/kg to 25 mCi/kg body weight, more preferably about 10 µCi/kg to 15 mCi/kg body weight. Generally, the total amount of multi-tyrosinated somatostatin analog delivered in a single dose is from about 100 mCi to 2,000 mCi, normally about 150 mCi to 1,500 mCi.

The efficacy of the therapy can be assessed by monitoring the levels of a biochemical marker associated with the condition (e.g., a somatostatin-regulatable factor), by in vivo imaging using radiolabeled multi-tyrosinated somatostatin analogs as described above, or by using conventional radiographic techniques. The dosage of multi-tyrosinated somatostatin analog can then be adjusted as appropriate, e.g., for therapy with non-radioactive multi-tyrosinated analogs (i.e., unmodified or modified, e.g., by halogenation) or for therapy with incremental doses of radiolabeled analogs of the invention.

Synthesis of six exemplary multi-tyrosinated somatostatin analogs

Six exemplary multi-tyrosinated somatostatin analogs were synthesized. The formulas of these analogs are shown in Table 2.

TABLE 2

Exemplary Multi-tyrosinated Somatostatin Analogs

WOC-2A
```
              ┌──────────────────────────────┐
D-Tyr—Cys—Tyr—D-Trp—Lys—Val—Cys—Thr—NH₂
```

WOC-2B
```
          ┌──────────────────────────────┐
Tyr—D-Tyr—Cys—Phe—D-Trp—Lys—Thr—Cys—Thr—NH₂
```

WOC-3A
```
              ┌──────────────────────────────┐
Tyr—Ala—D-Tyr—Cys—Tyr—D-Trp—Lys—Val—Cys—Thr—NH₂
```

WOC-3B
```
          ┌──────────────────────────────┐
Tyr—D-Tyr—Cys—Tyr—D-Trp—Lys—Val—Cys—Thr—NH₂
```

WOC-4
```
                       ┌──────────────────────────────┐
D-Tyr—Tyr—Tyr—D-Tyr—Cys—Phe—D-Trp—Lys—Thr—Cys—Thr—NH₂
```

WOC-8

```
D-Tyr
     \
      Lys
     /   \
D-Tyr     \
     \     \
      Lys   \
     /       \
D-Tyr         \
     \         \
      Lys       \
     /           \                 ┌──────────────────────────┐
D-Tyr             \                │                          │
                   Lys—D-Phe—Cys—Phe—D-Trp—Lys—Thr—Cys—Thr—NH₂
D-Tyr             /
     \           /
      Lys       /
     /         /
D-Tyr         /
     \       /
      Lys   /
     /     /
D-Tyr     /
     \   /
      Lys
     /
D-Tyr
```

Amino Terminus    Carboxy Terminus

Each of the multi-tyrosinated somatostatin analogs described above was prepared by reacting a neutralized benzhydrylamine-polystyrene resin with activated amino acids. Specifically, benzhydrylamine-polystyrene resin (Advanced ChemTech, Inc.) (1.2 g, 0.5 mmole) in the chloride ion form was placed in the reaction vessel of an Advanced ChemTech peptide synthesizer programmed to perform the following reaction cycle steps: (1) methylene chloride; (2) 33% trifluoroacetic acid in methylene chloride (two times for 1 hr and 25 min each); (3) methylene chloride; (4) ethanol; (5) methylene chloride; (6) 10% triethylamine in chloroform. The same reaction cycle steps were used in the production of each of the analogs described above.

The WOC-2A analog was prepared by first stirring the neutralized resin with Boc-O-benzyl-threonine and diisopropylcarbodiimide (1.5 mmole each) in methylene chloride for 1 h. The resulting amino acid resin was cycled through steps (1) to (6) in the above wash program. The following amino acids (1.5 mmole) each were then coupled successively by the same procedure: Boc-S-methylbenzyl-Cys, Boc-Val, Boc-N-benzyloxycarbonyl-lysine, Boc-D-Trp, Boc-O-dichlorobenzyl-Tyr, and Boc-S-methylbenzyl-Cys, and Boc-O-dichlorobenzyl-D-Tyr. After washing and drying, the completed resin having bound Boc-O-Dichlorobenzyl-D-tyrosine-S-methylbenzyl-cysteine-O-dichlorobenzyl-tyrosine-D-tryptophan-N-benzyloxycarbonyl-lysine-valine-S-methylbenzyl-cysteine-threonine weighed 1.78 g.

WOC-2A analog was released from the resin (1.78 g, 0.5 mmole) by mixing the amino acid resin with anisole (5 ml), dithiothreitol (100 mg) and anhydrous hydrogen fluoride (35 ml) at 0° C. and stirred for 45 min. Excess hydrogen fluoride was evaporated rapidly under a stream of dry nitrogen and free cyclic-(D-tyrosine-cysteine-tyrosine-D-tryptophan-lysine-valine-cysteine-threonine-NH₂) (WOC-2A) peptide precipitated and washed with ether.

The crude peptide was then dissolved in 500 ml of 90% acetic acid to which was added a concentrated solution of I₂/MeOH until a permanent brown color was observed. Excess I2 was removed by addition of ascorbic acid and the solution evaporated to a small volume which is applied to a column (2.5×90 cm) of Sephadex G-25 which is eluted with 50% AcOH. Fractions containing a major component as determined by UV absorption and thin layer chromatography were then pooled, evaporated to a small volume and applied to a column (1.5×70 cm) of Vydac octadecylsilane silica (10–15 µm). The analog was eluted with a linear gradient of acetonitrile in 0.1% trifluoroacetic acid in water. Fractions were examined by thin layer chromatography and analytical high performance liquid chromatography and pooled to give maximum purity. Repeated lyophilization of the solution from water yielded the desired product as a white, fluffy powder. The product was homogeneous as determined by high-pressure liquid chromatography (HPLC) and TLC. Amino acid analysis of an acid hydrolysate and MALD MS confirmed the composition of the octapeptide.

The WOC-2B analog was prepared by first stirring the neutralized resin with Boc-O-benzyl-threonine and diisopropylcarbodiimide (1.5 mmole each) in methylene chloride for 1 h. The resulting amino acid resin was cycled through steps (1) to (6) in the above wash program. The following amino acids (1.5 mmole) each were then coupled successively by the same procedure: Boc-S-methylbenzyl-Cys, Boc-O-benzyl-Thr, Boc-N-benzyloxycarbonyl-lysine, Boc-D-Trp, Boc-Phe, Boc-S-methylbenzyl-Cys, Boc-O-dichlorobenzyl-D-Tyr, and, Boc-O-dichlorobenzyl-Tyr. After washing and drying, the completed resin having bound Boc-O-dichlorobenzyl-tyrosine-O-dichlorobenzyl-D-tyrosine-S-methybenzyl-cysteine-phenylalanine-D-tryptophan-N-benzyloxycarbonyl-lysine-O-benzyl-threonine-S-methylbenzyl-cysteine-O-benzylthreonine weighed 1.78 g.

WOC-2B analog was released from the resin (1.78 g, 0.5 mmole) by mixing the amino acid resin with anisole (5 ml), dithiothreitol (100 mg) and anhydrous hydrogen fluoride (35 ml) at 0° C. and stirred for 45 min. Excess hydrogen fluoride was evaporated rapidly under a stream of dry nitrogen and free cyclic-(tyrosine-D-tyrosine-cysteine-phenylalanine-D-tryptophan-lysine-threonine-cysteine-threonine-$NH_2$) (WOC-2B) peptide precipitated and washed with ether.

The crude peptide was then dissolved in 500 ml of 90% acetic acid to which was added a concentrated solution of $I_2$/MeOH until a permanent brown color was observed. Excess $I_2$ was removed by addition of ascorbic acid and the solution evaporated to a small volume which is applied to a column (2.5×90 cm) of Sephadex G-25 which is eluted with 50% AcOH. Fractions containing a major component as determined by UV absorption and thin layer chromatography were then pooled, evaporated to a small volume and applied to a column (1.5×70 cm) of Vydac octadecylsilane silica (10–15 μm). The analog was eluted with a linear gradient of acetonitrile in 0.1% trifluoroacetic acid in water. Fractions were examined by thin layer chromatography and analytical high performance liquid chromatography and pooled to give maximum purity. Repeated lyophilization of the solution from water yielded the desired product as a white, fluffy powder. The product was homogeneous as determined by high-pressure liquid chromatography [HPLC] and TLC. Amino acid analysis of an acid hydrolysate and MALD MS confirmed the composition of the nonapeptide.

The cyclic(tyrosine-alanine-D-tyrosine-cysteine-tyrosine-D-tryptophan-lysine-valine-cysteine-threonine) (WOC-3A) analog was prepared by stirring the neutralized benzhydrylamine-polystyrene resin described above with Boc-O-benzyl-threonine and diisopropylcarbodiimide (1.5 mmole each) in methylene chloride for 1 h. The resulting amino acid resin was then cycled through steps (1) to (6) in the wash program described above. The following amino acids (1.5 mmole each) were then coupled successively by the same procedure: Boc-S-methylbenzyl-Cys, Boc-Val, Boc-N-benzyloxycarbonyl-lysine, Boc-D-Trp, Boc-O-dichlorobenzyl-Tyr, Boc-S-methylbenzyl-Cys, Boc-O-dichlorobenzyl-D-Tyr, Boc-Ala, and Boc-O-dichlorobenzyl-Tyr. After washing and drying, the resulting Boc-O-dichlorobenzyl-tyrosine-alanine-O-dichlorobenzyl-D-tyrosine-S-methybenzyl-cysteine-dichlorobenzyl-tyrosine-D-tryptophan-N-benzyloxycarbonyl-lysine-valine-S-methybenzyl-cysteine-O-benzyl-threoninebenzhydrylamine peptide resin weighed 2.1 g.

The amino acid resin was then subjected to HF cleavage and $I_2$ cyclization as described above. Column purification as described yielded the cyclic(tyrosine-alanine-D-tyrosine-cysteine-tyrosine-D-tryptophan-lysine-valine-cysteine-threonine) (WOC-3A) compound. WOC-3 was homogeneous as determined by HPLC and TLC. Amino acid analysis of an acid hydrolysate and MALD MS confirmed the composition of the WOC-3A peptide.

The cyclic(tyrosine-D-tyrosine-cysteine-tyrosine-D-tryptophan-lysine-valine-cysteine-threonine) (WOC-3B) analog was prepared by stirring the neutralized benzhydrylamine-polystyrene resin described above with Boc-O-benzyl-threonine and diisopropylcarbodiimide (1.5 mmole each) in methylene chloride for 1 h. The resulting amino acid resin was then cycled through steps (1) to (6) in the wash program described above. The following amino acids (1.5 mmole each) were then coupled successively by the same procedure: Boc-S-methylbenzyl-Cys, Boc-Val, Boc-N-benzyloxycarbonyl-lysine, Boc-D-Trp, Boc-O-dichlorobenzyl-Tyr, Boc-S-methylbenzyl-Cys, Boc-O-dichlorobenzyl-D-Tyr, and Boc-0-dichlorobenzyl-Tyr. After washing and drying, the amino acid resin was subjected to HF cleavage and $I_2$ cyclization as described above. Column purification as described yielded the cyclic(tyrosine-D-tyrosine-cysteine-tyrosine-D-tryptophan-lysine-valine-cysteine-threonine) (WOC-3B) compound. WOC-3B was homogeneous as determined by HPLC and TLC. Amino acid analysis of an acid hydrolysate and MALD MS confirmed the composition of the WOC-3B peptide.

The cyclic D-tyrosine-(tyrosine-tyrosine-D-tyrosine-cysteine-phenylalanine-D-tryptophan-lysine-threonine-cysteine-threonine) (WOC-4) analog was prepared by stirring the neutralized benzhydrylamine-polystyrene resin described above with Boc-O-benzyl-threonine and diisopropylcarbodiimide (1.5 mmole each) in methylene chloride for 1 h. The resulting amino acid resin was then cycled through steps (1) to (6) in the wash program described above. The following amino acids (1.5 mmole each) were then coupled successively by the same procedure: Boc-S-methylbenzyl-Cys, Boc-O-benzyl-Thr, Boc-N-benzyloxycarbonyl-lysine, Boc-D-Trp, Boc-Phe, Boc-S-methylbenzyl-Cys, Boc-O-dichlorobenzyl-D-Tyr, Boc-O-dichlorobenzyl-Tyr, Boc-O-dichlorobenzyl-Tyr, and Boc-O-dichlorobenzyl-D-Tyr. After washing and drying, the amino acid resin was subjected to HF cleavage and $I_2$ cyclization as described above. Column purification as described yielded the cyclic(D-tyrosine-tyrosine-tyrosine-D-tyrosine-cysteine-phenylalanine-D-tryptophan-lysine-threonine-cysteine-threonine) (WOC-4) peptide resin was released from the resin by HF cleavage and $I_2$ cyclization as described. Column purification as described yielded homogenous WOC-4 compound as determined by HPLC and TLC. Amino acid analysis of an acid hydrolysate and MALD MS confirmed the composition of the WOC-4 peptide.

The cyclic[(D-tyrosine)$_8$-(lysine)$_4$-(lysine)$_2$-lysine-cysteine-phenylalanine-D-tryptophan-lysine-threonine-cysteine-threonine] (WOC-8) peptide was prepared by stirring the neutralized resin described above with Boc-O-benzyl-threonine and diisopropylcarbodiimide (0.75 mmole each) in methylene chloride for 1 h and the resulting amino acid resin is then cycled through steps (1) to (6) in the above wash program. The following amino acids (0.75 mmole) were then coupled successively by the same procedure: Boc-S-methylbenzyl-Cys, Boc-O-benzyl-Thr, Boc-N-benzyloxycarbonyl-lysine, Boc-D-Trp, Boc-Phe, and Boc-S-methylbenzyl-Cys, Boc-D-Phe and Bis-Boc-Lys. The resin was then deprotected, neutralized and coupled with Boc-Tyr (6 mmole) and DIC (6 mmole) in the presence of 1-hydroxybenzotriazole (6 mmole). After washing and drying, the completed (Boc-D-tyrosine)$_8$-(lysine)$_4$-(lysine)$_2$-lysine-D-phenylalanine-S-methybenzyl-cysteine-phenylalanine-D-tryptophan-N-benzyloxycarbonyl-lysine-Boc-O-benzyl-Thr-S-methybenzyl-cysteine-O-benzyl-threonine-benzhydrylamine resin weighed 1.53 g.

The WOC-8 was released from the resin by HF cleavage and $I_2$ cyclization as described. Column purification yielded homogeneous WOC-8 as determined by HPLC and TLC. Amino acid analysis of an acid hydrolysate and MALD MS confirmed the composition of the WOC-8 peptide.

As is evident from the description above, multiple tyrosine residues can be incorporated at the N-terminus of the somatostatin analogs. The tyrosine residues can be added to the analog so as to form a symmetrically branching structure, as exemplified by the compound WOC-8. Alternatively, the somatostatin analogs can be N-terminally extended in an asymmetrical fashion (i.e., the variables q and s in the formula above are not equal). Asymmetrically branched N-terminal extensions can be produced by using combinations of the lysine derivative, $N^\alpha$-Boc,$N^\epsilon$-FMOC-Lys. This lysine derivative can be deprotected either at the $N^\alpha$ position by TFA treatment, or at the $N^\epsilon$ position by treatment with piperidine/DMF solutions. Thus virtually any combination of tyrosine residues can be added to the N-terminus to produce symmetrically or asymmetrically the branching chains.

Radioiodination of the WOC-2A, WOC-2B, WOC-3A, WOC-3B, WOC-4, and WOC-8 multi-tyrosinated somatostatin analogs Radiolabeling of the multi-tyrosinated somatostatin analogs can be accomplished by a variety of radiolabeling protocols well known in the art.

Radioiodination of WOC-2A, WOC-3A, WOC-3B, WOC-4, and WOC-8 was accomplished by first adding 0.5M potassium/sodium phosphate buffer, pH 7.0 (0.1 ml) to a 12×75 m polypropylene tube containing 1 mCi of $^{125}$I sodium iodide (10 µl) and mixing. Subsequently, 5 µg of a multi-tyrosinated somatostatin analog and 100 µl of 0.05M potassium/sodium phosphate buffer, pH 7.0 were added to the mixture and the solution again mixed. Immediately thereafter, 5.7 µg of chloramine T (10 µl) was added to the solution and 60 seconds later the reaction was terminated by addition of 57 µg of metabisulfite (100 µl). Each step was continually bounced-mixed to ensure rapid and proper mixing. Thirty seconds after the addition of sodium metabisulfite, 2.0 ml of 0.005% injectable human serum albumin (HSA) in 0.05M acetic acid was added to the reaction vessel.

A SEP-PAK C-18 column (Milipore Corporation, Milford, Mass.) was sterilized with 5 ml of 70% ethanol, activated with 5 ml of 2-propanol, and rinsed with 12.5 ml of HPLC purified water. The reaction mixture was applied to this column and the column was washed with 5 ml of HPLC purified water. The column was then subsequently washed with 5 ml of 0.05M acetic acid. The labeled analog was eluted with 5 ml of 96% ethanol. The final eluate was collected in a 13×100 mm non-HSA coated polypropylene tube. The percent of the total radioactivity recovered for each eluate was counted with a radioisotope calibrater under a gentle stream of nitrogen at 40° C. The dried radiolabeled analog was reconstituted in 115 µl of 100 mM potassium phosphate, pH 6.9:methanol (40:60), and incubated at 40° C. for 15 min with intermittent vortexing to ensure complete reconstitution. The redissolved, labeled material was centrifuged for two minutes to remove any remaining particulate matter.

The radiolabeled analogs were then further purified by high pressure liquid chromatography (HPLC). The HPLC system was first equilibrated with 100 mM potassium phosphate, pH 6.9:methanol:water (20:30:50) for 18 min at 1.0 ml/min. The reconstituted radiolabeled analog was loaded onto the column and purified at a flow rate of 1.0 ml/mn for 20 min. The initial mobile phase conditions were held for 1 min after sample injections, then changed to 100 mM potassium phosphate, pH 6.9:methanol (40:60) over 2 min. Fractions of 0.2 ml were collected in 13×100 mm HSA-coated polypropylene tubes. The radioactivity of each fraction was counted in a radioisotope calibrater. Chromatograms for UV and radioisotope detectors were processed and recorded using MILLENIUM™2010 Chromatography Manager Software. The purified monoiodinated $^{125}$-I labeled analog was evaporated to dryness in a 40° C. waterbath using a gentle flow of nitrogen. The dried, purified, and radiolabeled analog residue was reconstituted in 2.0 ml of 0.9% sodium chloride and 0.05M acetic acid. The analog solution was then passed through a low-protein binding 0.22 micron MILLEX-GV filter coated with 2% HSA and flushed with 0.9% sodium chloride. This technique allowed rapid separation of the specific radiolabeled specimen peak from unwanted waste.

An aliquot of this filter-sterilized compound was incubated in soybean casein digest at 35° C. for up to 14 days and thioglycolate media at 22° C. for up to 14 days to test for bacterial growth. Endotoxin testing was performed using the E-Toxate kit (Sigma, St. Louis, Mo.). Solutions that demonstrated no bacterial growth at 48 hours and showed no detectable endotoxin were considered safe for human use.

All specimen activity (µCi) was measured in a dose calibrator at least 30 minutes prior to intravenous injection. Radiolabeled peptide was injected through a peripheral arm vein in a free-flowing intravenous line. One week after labeling, only 30% of the $^{131}$I-labeled multi-tyrosinated peptides WOC-3A and WOC-3B compounds stored in saline had degraded.

Somatostatin receptor binding and biological activity assays

The human neuroblastoma cell line IMR32 (ATCC CCL 127), which expresses type 2 somatostatin receptors (SSTR2), was used in somatostatin receptor binding assays. The IMR32 cells were maintained in minimal essential media (MEM) supplemented with 15% heat-inactivated fetal bovine serum, 100 U/ml penicillin, 100 µg/ml streptomycin and nonessential amino acids. Cultured cells were harvested in a buffer containing 20 mM HEPES, 2 mM $MgCl_2$, 5 mM EDTA, 1 mM 2-mercaptoethanol, 150 mM NaCl, and 50 µg/ml phenylmethylsulfonylfluoride (PMSF), (pH 7.4) at a concentration of 1×10$^6$ cells/ml. Cell membranes were prepared according to the method of O'Dorisio, M. S. et al., *Cell Growth and Differentiation*, 5:1–8, 1994. Membrane fractions were prepared by differential centrifugation and the membranes resuspended in buffer and stored at −80° for receptor binding studies.

Binding assays were carried out according to the method of O'Dorisio et al., supra. Briefly, somatostatin receptor binding assays were performed in media containing 50 mM HEPES, 10 mM $CaCl_2$, 5 mM $MgCl_2$, 50 ng/ml bacitracin, 200 KIU/ml Aprotinin, 0.02 µg/ml PMSF and 0.5% bovine serum albumin. Specific binding of both $^{125}$I-multi-tyrosinated somatostatin analogs and $^{125}$I-native somatostatin (S-14) were determined. IMR32 membrane fractions (100–150 µg) were incubated with 0.015 pM $^{125}$I-multi-tyrosinated analog or $^{125}$I-somatostatin with or without increasing concentrations of unlabeled ligand in a shaking, temperature controlled water-bath (17° C.) for 30 minutes. The reaction was terminated by centrifugation at 11,000×G for 3 minutes. Supernatant fluid was aspirated and the radioactivity of bound ligand in the pellet quantified in a gamma counter.

Specific binding was calculated using the difference between total and non-specific (in the presence of 1 µM unlabeled ligand) binding. Equilibrium dissociation constants ($K_D$) and the maximal number of binding sites ($B_{max}$) were determined using seven concentrations of unlabeled peptide in a competitive binding curve and calculated using a computerized nonlinear least squares fit to the mass-law equation of Munson and Rodbard, Munson, P. J. et al., *Anal. Biochem.*, 107:220–239, 1980, as modified by McPhearson, G. A., *J. of Pharm. Meth.*, 14:213–228, 1985. The results of these assays with WOC-2A, WOC-2B, WOC-3A, WOC-3B, WOC-4, and WOC-8 are shown in Table 3. Binding curves for native somatostatin, WOC-2A, and WOC-3B are shown in FIGS. 2A, 2B, and 2C, respectively. FIG. 2D is a graph of a composite curve showing relative affinities of native somatostatin, WOC-2A, and WOC-3B, and the commercially available somatostatin analog LANREOTIDE®.

TABLE 3

| | GH release ($IC_{50}$, nM) | Somatostatin Receptor Binding (IMR32 membranes) (Kd, nM) |
|---|---|---|
| Somatostatin | 0.46 ± 0.04 (18)* | 0.23 ± 0.15 |
| LANREOTIDE ® | 0.40 ± 0.10 (3) | 1.05 ± 0.51 |
| WOC-2A | 4.84 ± 0.58 (7) | 5.73 ± 0.22 |
| WOC-2B | — | 1.2 |
| WOC-3A | 0.96 ± 0.01 (2) | 1.93 ± 0.35 |
| WOC-3B | 0.66 ± 0.06 (8) | 1.14 ± 0.28 |
| WOC-4 | — | 1.0 |
| WOC-8 | 2.46 ± 0.69 (6) | 0.69 ± 0.42 |

*Number of samples tested for GH release.

Exposure of IMR-32 membranes to radiolabeled somatostatin analog WOC-3A resulted in high levels of total binding. When membranes having bound radiolabeled WOC-3A were incubated in the presence of a 10,000-fold excess of unlabeled WOC-3A or native somatostatin, no radioactivity was displaced. These results indicate that halogenated, multi-tyrosinated analogs bind somatostatin receptors in an irreversible (or nearly irreversible) manner, and imply that these somatostatin analogs can be internalized into the cell.

The multi-tyrosinated somatostatin analogs were also tested for their ability to inhibit release of growth hormone (GH) from acutely dispersed rat pituitary cells, which express SSTR2. Pituitaries from adult Charles River CD male rats (Wilmington, Mass.) housed under controlled conditions (lights on from 0500–1900 hrs), were dispersed and cultured using aseptic technique as previously described with modifications (Hoefer et al., *Mol. Cell Endocrinol.*, 35:229, (1984); Ben-Jonathan et al., i Methods Enzymol., 103:249, (1983); and Heiman et al., *Endocrinology*, 116:410, (1985).

Briefly, pituitaries were removed from decapitated rats, sectioned, and then placed in a siliconized, liquid scintillation vial containing 2 ml 0.2% trypsin (Worthington Biochemicals, Freehold, N.J.) in sterile-filtered Krebs-Ringer bicarbonate buffer supplemented with 1% bovine serum albumin, 14 mM glucose, modified Eagle medium (MEM) vitamin solution and MEM amino acids (Gibco Laboratories, Grand Island, N.Y.) (KRBGA). All glassware was siliconized as described by Sayers et al., *Endocrinology*, 88:1063, (1971). The pituitary fragments were incubated in a water bath for 35 min at 37° C. with agitation. The vial contents were then poured into a scintillation vial containing 2 ml 0.1% DNase (Sigma Chemical Co., St. Louis, Mo.) in KRBGA and incubated for 2 min at 37° C. with agitation. After incubation the tissue was decanted into a 15 ml centrifuge tube and allowed to settle. The medium was discarded, and the pituitary sections were washed 3 times with 1 ml fresh KRBGA. The cells were dispersed in 2 ml 0.05% LBI (lima bean trypsin inhibitor, Worthington Biochemicals) by gently drawing the fragments into and expelling them out of a siliconized, fire-polished Pasteur pipette. Dispersed cells were filtered through a 630 μm diameter Nylon mesh (Tetko, Elmsford, N.Y.) into a fresh 15 ml centrifuge tube. An additional 2 ml of 0.05% LBI solution was used to rinse the first tube and was transferred to the second tube with filtering.

The dispersed cells were further diluted with approximately 15 ml sterile-filtered Dulbecco's modified Eagle medium (GIBCO), supplemented with 2.5% fetal calf serum (GIBCO), 3% horse serum (GIBCO), 10% fresh rat serum (stored on ice for no longer than 1 h) from the pituitary donors, 1% MEM non-essential amino acids (GIBCO), gentamycin (10 ng/ml; Sigma) and nystatin (10,000 U/ml; GIBCO). The cells were poured into a 50 ml round-bottomed glass extraction flask with a large diameter opening, counted with a hemacytometer (approximately 2,000,000 cells per pituitary), and randomly plated at a density of 200,000 cells per well (Co-star cluster 24; Rochester Scientific Co., Rochester, N.Y.). The plated cells were maintained in Dulbecco's medium in a humidified atmosphere of 95% air and 5% $CO_2$ at 37° C. for 4 days to 5 days.

In preparation for a hormone challenge, the cells were washed 3 times with medium 199 (GIBCO) to remove old medium and floating cells. Each dose of somatostatin or analog (diluted in siliconized test tubes) was tested in the presence of 1 nM GRF(1-29)$NH_2$ in triplicate wells in a total volume of 1 ml medium 199 containing 1% BSA (fraction V; Sigma). After 3 h at 37° C. in an air/carbon dioxide atmosphere (95/5%), the medium was removed and stored at –20 ° C. until assayed for hormone content. $IC_{50}$'s (a concentration that provides half-maximal inhibition of GH release) were calculated using the computer program *SigmaPlot* (Jandel Scientific, San Rafael, Calif.).

The results of the GH release inhibition assays are shown in Table 3. All multi-tyrosinated somatostatin analogs tested inhibited GH release. The direct correlation between somatostatin receptor binding and inhibition of growth hormone release between somatostatin receptor binding and inhibition of growth hormone release is discussed in Rayner, *Mol. Pharmacol.*, 43:838–844, 1993.

The above data demonstrate that multi-tyrosinated peptide analogs not only bind to somatostatin receptors, but also retain the biological activity of somatostatin.

Example of in vivo diagnosis and therapy in a human patient

HC is a 75-year-old white male diagnosed with bronchioloalveolar carcinoma of the lung approximately four years ago. HC underwent a right upperlobectomy and intensive chemotherapy with multiple agents. His disease was progressive through these treatments. An $^{111}$In-labeled pentetreotide (OCTREOSCAN®) scan showed multiple tumors throughout both lung fields. Based on this finding, the patient was placed on subcutaneous octreotide acetate (2 mg/day) first administered by three separately spaced injections and subsequently administered by continuous subcutaneous infusion by battery-operated pump. The patient tolerated this therapy well and initially had a 25% decrease in his tumor volume. Over the ensuing several months the patient's tumors progressed despite this therapy.

The octreotide acetate therapy was terminated and one week later the patient again underwent $^{111}$In-pentetreotide (Octreoscan®) scanning. This scan showed that HC had developed approximately 15 brain metastasis and that his lung tumor continued to scan positive. No other additional sites of metastases were discovered.

After careful consideration and consultation with the patient's local medical doctor and his local medical oncologist, it was decided that this patient had exhausted all conventional treatment options. Because the patient's tumor bound radiolabeled somatostatin analogs as determined by the [111]I-pentetreotide scan, therapy with radiolabeled somatostatin analogs can be efficacious as these analogs would deliver the radioactivity directly to the tumor. Compassionate-need use of radiolabeled somatostatin analogs was initiated immediately.

The multi-tyrosinated somatostatin analog WOC-3A was radiolabeled and its binding to somatostatin receptors was tested as described above. A batch of $^{131}$I WOC-3A (1.6 mCi) was made (Iso-Tex Corporation, Friendswood, TX) and its sterility and pyrogenicity tested at Iso-Tex. Radiolabeled WOC-3A was injected intravenously and the pharmacokinetics and biodistribution of the radiolabeled compound were calculated. The tumor/normal tissue ratio of distribution of radiolabeled WOC-3A was approximately 3:1 to 6:1.

Following injection of 1.6 mCi of $^{131}$I WOC-3A, the patient underwent three days of nuclear medicine scanning using a 3-headed SPECT camera as well as an ADAC camera. In addition, whole body radiation counts were obtained to calculate whole-body loss of radioisotope over the three day period. These studies indicated that a dose of 1,500 mCi can provide a tumoricidal radiation therapy dose, yet be within normal tissue tolerance for radiation exposure for all tissues except bone marrow. Bone marrow would receive in excess of 450 rads (a dose requiring bone marrow transplantation in 50% of patients). Thus, in preparation for bone marrow transplantation, the patient underwent bone marrow harvest to provide cells for reinfusion after WOC-3 therapy and sufficient clearance of the radiolabeled analog from the patient's circulation.

The patient was given 1,610 mCi of a radiolabeled somatostatin analog preparation by intravenous infusion over a one hour period. The analog preparation contained 582 mCi, 758 mCi WOC-3A, and 221 mCi WOC-3B. To prevent the accumulation of excreted $^{131}$I analog in the gut, a Dobhoff tube was placed in the duodenum. The tube was flushed with 500 cc/hr of Go-Lytely®. During the entire time of the Go-Lytely® administration, the patient was sitting on a toilet designed to continuously flush to dilute the radioactive waste as rapidly as possible. This treatment was carried out at the Medical Center of Louisiana at New Orleans (Charity Hospital) in a lead-lined room in an isolated section of the hospital. Airborne free $^{131}$I as extracted from the air using a charcoal filter in a series with a UHEPA filter. All personnel radiation exposure was continuously monitored with personal dosimeters. The State of Louisiana Nuclear Regulatory Agency supplied two observers to ensure personnel safety.

Six days following the administration of the radiolabeled somatostatin analog, the patient's total body counts had decreased to levels allowing a nuclear medicine scan of his brain. Counts in his chest as this point were still too high to allow scanning.

Subsequently, the patient developed a cardiac arrhythmia (premature atrial contractions with a rapid ventricular response) and required digitalization. The patient was transferred to the medical intensive care unit and was subsequently shown to have had a myocardial infarction by enzymes and EKG changes. His medical history included two significant myocardial infarctions, the most recent of which was approximately five months prior to this therapy. On the seventh day following $^{131}$I somatostatin analog, the patient experienced a lethal cardiac arrhythmia and expired. An autopsy was performed seven days after injection and normal/tumor tissue harvested for determination of the number of mCi of $^{131}$I in each gram of tissue. In addition, a standard autopsy protocol for histology was performed. Biopsies from brain, muscle, and thyroid were subjected to autoradiography to allow exposure of silver grains by $^{131}$I-WOC3. Silver grain deposition was observed in brain, indicating that the $^{131}$I-WOC3 penetrated the blood-brain barrier. Silver grain deposition was also observed in thyroid, but was not observed in muscle. This later observation indicates that $^{131\text{ }I\text{-}WOC}$3 localization is tissue-specific and correlates with tissue-specific expression of somatostatin receptors.

Gross findings at autopsy showed a severe coronary artery disease with "stove pipe" coronary arteries, a number of old cardiac scars consistent with old myocardial infarctions and evidence of a recent sub-endocardial infarction. No evidence of significant cerebral edema or evidence of other organ dysfunction was discovered.

The normal brain and brain tumors were clearly distinct from one another and the ratio of mCi/gm of tissue in brain tumor/normal brain was 12:1. No significant radioactivity was found in the heart. The diffuse nature of the patient's miliary lung tumors made it very difficult to differentiate normal lung from tumor-containing lung. Thus, determination of tumor/normal tissue ratios in the lung were impossible.

Subsequently, tumor and normal tissue specimens were examined by autoradiography. Significant amounts of radioactivity were associated within the brain tumor and a limited amount of radioactivity was distributed within normal brain tissue. Although these results cannot be attributed solely to the multi-tyrosinated analogs due to the presence of LAN-REOTIDEυ in the injected preparation, the ratios of tumor to normal tissue binding are consistent with pre-operative scanning diagnostics using WOC-3A alone.

Other embodiments of the invention are within the following claims.

What is claimed is:

1. A compound having a formula selected from the group consisting of:

a) $(Y)_{n+1}P$,
b) $(Y)_n$—Ala—Y—P, and c) 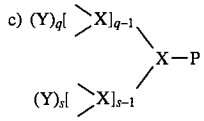

wherein

P is a somatostatin peptide analog which binds to a somatostatin receptor;

Y is D-tyrosine, L-tyrosine, or desamino-tyrosine;

n is an integer from 1 to 32, inclusive;

each q, independently, is an integer from 1 to 32, inclusive, each s, independently, is an integer from 1 to 32, inclusive, where q and s can be the same or different, and X is of the formula D—NH$_2$—CH(CH$_2$)$_m$NH$_2$—CO$_2$H or L—NH$_2$—CH(CH$_2$)$_m$NH$_2$—CO$_2$H, wherein m is an integer from 1 to 10, inclusive.

2. The compound according to claim 1, wherein P is selected from the group consisting of:

a) Cys-Tyr-D-Trp-Lys-Val-Cys-Thr-NH$_2$, b) Cys-Phe-D-Trp-Lys-Thr-Cys-Thr-NH$_2$, and c) Cys-Tyr-D-Trp-Lys-Thr-Cys-Thr(ol).

3. The compound according to claim 1, wherein X is lysine.

4. The compound according to claim 1, wherein the compound comprises a halogen atom bound to a D-tyrosine, L-tyrosine, or desamino-tyrosine of the compound.

5. The compound according to claim 4, wherein said halogen atom is radioactive.

6. The compound according to claim 5, wherein said radioactive halogen atom is $^{123}$I, $^{124}$I, $^{125}$I, $^{129}$I, or $^{131}$I.

7. A compound having a formula selected from the group consisting of:

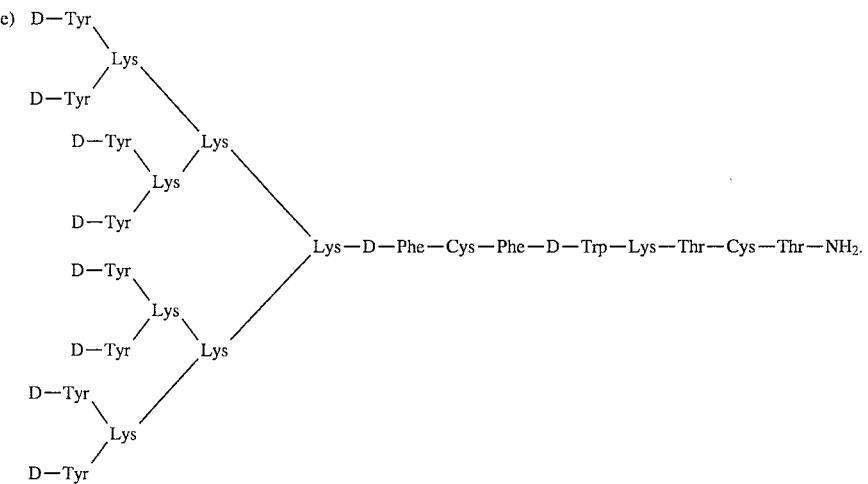

8. The compound according to claim 7, further comprising a halogen atom bound to a tyrosine residue.

9. The compound according to claim 8, wherein the tyrosine residue is selected from the group consisting of L-tyrosine, D-tyrosine, and desamino tyrosine.

10. The compound according to claim 8, wherein said halogen atom is radioactive.

11. The compound according to claim 9, wherein said radioactive halogen atom is selected from the group consisting of: $^{123}I$, $^{124}I$, $^{125}I$, $^{129}I$, and $^{131}I$.

12. A pharmaceutical composition comprising:
a compound according to claim 1; and
a pharmaceutically acceptable carrier.

* * * * *

UNITED STATES PATENT AND TRADEMARK OFFICE
CERTIFICATE OF CORRECTION

PATENT NO. : 5,597,894
DATED : January 28, 1997
INVENTOR(S) : David H. Coy, Eugene A. Woltering, M. Sue O'Dorisio, Thomas M. O'Dorisio, and William A. Murphy It is certified that error appears in the above-indentified patent and that said Letters Patent is hereby corrected as shown below:

Title page; col. 2, after "McPherson, 'Analysis of radioligand...'", correct the spelling of "experiments";

Col. 11, line 62, replace "abut" with --about--;

Col. 19, line 38, replace "analoogs" with --analogs--;

Col. 22, line 47, replace "Excess 12" with --Excess $I_2$--;

Col. 27, line 33, delete "i" before "Methods Enzymol.";

Col. 29, line 63, replace "$^{131}I\text{-WOC}_3$" with --$^{131}$I-WOC3--;

Col. 30, line 19, replace "LANREOTIDEυ" with --LANREOTIDE™--;

UNITED STATES PATENT AND TRADEMARK OFFICE
CERTIFICATE OF CORRECTION

Page 2 of 3

PATENT NO. : 5,597,894
DATED : January 28, 1997
INVENTOR(S) : David H. Coy, Eugene A. Woltering, M. Sue O'Dorisio, Thomas M. O'Dorisio, and William A. Murphy It is certified that error appears in the above-indentified patent and that said Letters Patent is hereby corrected as shown below:

Col. 31, claim 7, correct the formula as shown below as follows:

a) Tyr-D-Tyr-Cys-Phe-D-Trp-Lys-Thr-Cys-Thr-NH$_2$,
b) Tyr-Ala-D-Tyr-Cys-Tyr-D-Trp-Lys-Val-Cys-Thr-NH$_2$,
c) Tyr-D-Tyr-Cys-Tyr-D-Trp-Lys-Val-Cys-Thr-NH$_2$,
d) D-Tyr-Tyr-Tyr-D-Tyr-Cys-Phe-D-Trp-Lys-Thr-Cys-Thr-NH$_2$,

UNITED STATES PATENT AND TRADEMARK OFFICE
CERTIFICATE OF CORRECTION

PATENT NO. : 5,597,894
DATED : January 28, 1997
INVENTOR(S) : David H. Coy, Eugene A. Woltering, M. Sue O'Dorisio, Thomas M. O'Dorisio, and William A. Murphy It is certified that error appears in the above-indentified patent and that said Letters Patent is hereby corrected as shown below:

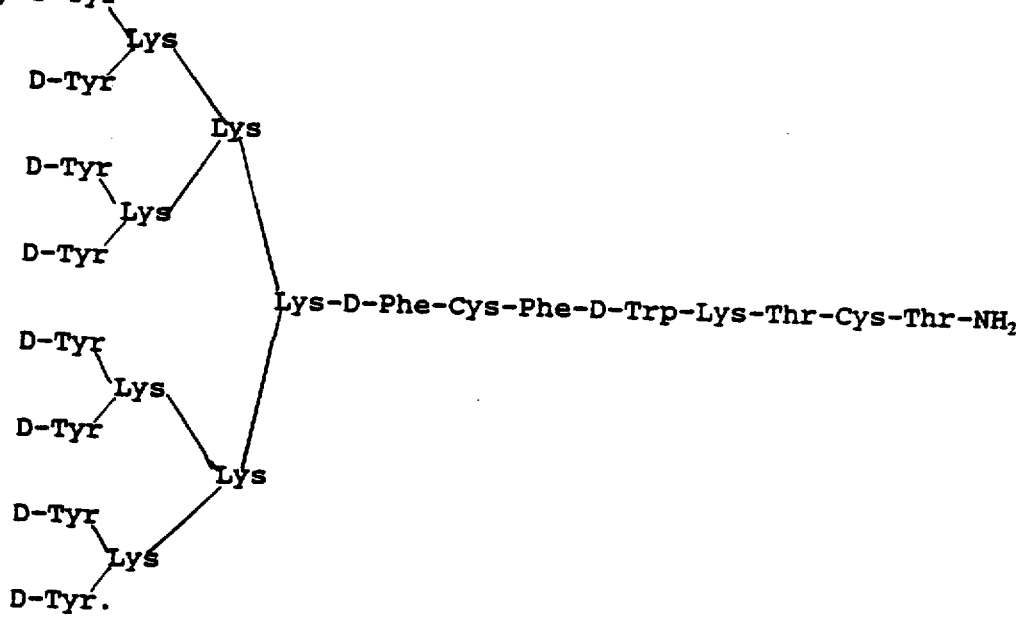

Signed and Sealed this

Twenty-sixth Day of August, 1997

Attest:

BRUCE LEHMAN

Attesting Officer

Commissioner of Patents and Trademarks